(12) United States Patent
Ziemer et al.

(10) Patent No.: US 8,748,343 B2
(45) Date of Patent: Jun. 10, 2014

(54) HERBICIDE/SAFENER COMBINTIONS

(75) Inventors: Frank Ziemer, Kriftel (DE); Lothar Willms, Hofheim (DE); Hermann Bieringer, Eppstein (DE); Erwin Hacker, Hochheim (DE)

(73) Assignee: Bayer Cropscience AG, Monheim (DE)

( * ) Notice: Subject to any disclaimer, the term of this patent is extended or adjusted under 35 U.S.C. 154(b) by 0 days.

(21) Appl. No.: 13/601,247

(22) Filed: Aug. 31, 2012

(65) Prior Publication Data

US 2012/0322657 A1 Dec. 20, 2012

Related U.S. Application Data

(60) Division of application No. 11/246,790, filed on Oct. 7, 2005, now abandoned, which is a continuation of application No. 09/856,188, filed as application No. PCT/EP99/08470 on Nov. 5, 1999, now abandoned.

(30) Foreign Application Priority Data

Nov. 21, 1998 (DE) .................................. 198 53 827

(51) Int. Cl.
| | | |
|---|---|---|
| A01N 25/26 | (2006.01) | |
| A01N 25/32 | (2006.01) | |
| A01N 43/36 | (2006.01) | |
| A01N 43/80 | (2006.01) | |
| A01N 37/10 | (2006.01) | |

(52) U.S. Cl.
USPC ........... 504/100; 504/106; 504/138; 504/271; 504/318

(58) Field of Classification Search
None
See application file for complete search history.

(56) References Cited

U.S. PATENT DOCUMENTS

| | | | |
|---|---|---|---|
| 5,334,753 A | 8/1994 | Bennetau et al. | |
| 5,441,922 A | 8/1995 | Ort et al. | |
| 5,506,195 A * | 4/1996 | Ensminger et al. | 504/350 |
| 5,516,750 A * | 5/1996 | Willms et al. | 504/106 |
| 5,561,100 A | 10/1996 | Hagen et al. | |
| 5,627,131 A | 5/1997 | Shribbs et al. | |
| 5,631,210 A | 5/1997 | Tseng et al. | |
| 5,650,533 A | 7/1997 | Roberts et al. | |
| 5,656,573 A | 8/1997 | Roberts et al. | |
| 5,747,424 A | 5/1998 | Roberts et al. | |
| 5,804,432 A | 9/1998 | Knapp et al. | |
| 5,804,532 A | 9/1998 | Cain et al. | |
| 5,859,283 A | 1/1999 | Cramp et al. | |
| 5,905,057 A | 5/1999 | Forget et al. | |
| 6,013,805 A | 1/2000 | Hawkins et al. | |
| 6,235,682 B1 | 5/2001 | Penner et al. | |
| 6,297,198 B1 | 10/2001 | Lee et al. | |
| 6,489,267 B1 | 12/2002 | Ruegg et al. | |
| 6,746,987 B2 | 6/2004 | Ruegg et al. | |
| 7,141,531 B2 | 11/2006 | Willms et al. | |
| 2001/0044382 A1 | 11/2001 | Ruegg et al. | |
| 2006/0030485 A1 | 2/2006 | Ziemer et al. | |
| 2010/0130362 A1 * | 5/2010 | Satchivi et al. | 504/105 |

FOREIGN PATENT DOCUMENTS

| | | |
|---|---|---|
| CA | 2334955 | 10/2011 |
| DE | 4316880 | 11/1993 |
| DE | 4331448 | 3/1995 |
| DE | 440354 | 5/1996 |
| DE | 19711953 | 9/1997 |

(Continued)

OTHER PUBLICATIONS

Sprague et al., "Enhancing the Margin of Selectivity of RPA 201772 in Zea mays with Antidotes," Weed Science, vol. 47, (1999), pp. 492-497.

(Continued)

*Primary Examiner* — Alton Pryor
(74) *Attorney, Agent, or Firm* — Frommer Lawrence & Haug LLP

(57) ABSTRACT

There are described herbicidal compositions which comprise at least one herbicidally active compound of the formula (I) and at least one crop-plant-protecting compound as safener.

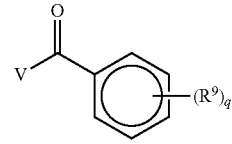

(I)

In this formula (I), V is an optionally substituted radical selected from the group consisting of isoxazol-4-yl, pyrazol-4-yl, cyclohexane-1,3-dion-2-yl and 3-oxopropionitril-2-yl and $R^9$ is nitro, amino, halogen or a carbon-containing radical. The group of the safeners contains, for example, 2,4-D, cyometrinil, dicamba, dymron, fenclorim, flurazole, fluxofenim, lactidichlor, MCPA, mecoprop, MG-191, oxabetrinil, methyl diphenylmethoxyacetate,
1-[4-(N-2-methoxybenzoylsulfamoyl)phenyl]-3-methylurea,
1,8-naphthalaic anhydride,
1-[4-(N-2-methoxybenzoylsulfamoyl)phenyl]-3,3-dimethylurea,
1-[4-(N-4,5-dimethylbenzoylsulfamoyl)phenyl]-3-methylurea,
1-[4-(N-naphthoylsulfamoyl)phenyl]-3,3-dimethylurea,
(4-chlorophenoxy)acetic acid, 4-(2,4-dichlorophenoxy)butyric acid,
4-(4-chloro-o-tolyloxy)butyric acid, 4-(4-chlorophenoxy) butyric acid, in each case their acids and esters, N-acylsulfonamides, N-acylsulfamoylbenzamides, in each case, if appropriate, also in salt form and in each case optionally substituted 1-phenylpyrazoline, 1-phenylpyrazole, 1-phenyltriazole, 5-phenylisoxazoline and 5-phenylmethylisoxazoline-3-carboxylic esters and 2-(8-quinolinyloxy)acetic acid derivatives.

11 Claims, No Drawings

(56) References Cited

FOREIGN PATENT DOCUMENTS

| | | |
|---|---|---|
| DE | 19853827 | 5/2000 |
| EP | 0298680 | 1/1989 |
| EP | 0496631 | 7/1992 |
| EP | 0551650 | 7/1993 |
| EP | 0918056 | 5/1999 |
| HU | P9202531 | 6/1996 |
| HU | P9301669 | 5/1997 |
| HU | P9300293 | 2/2000 |
| HU | P9202532 | 7/2000 |
| WO | WO 95/07897 | 3/1995 |
| WO | WO 96/14747 | 5/1996 |
| WO | WO 96/21357 | 7/1996 |
| WO | WO 97/34485 | 9/1997 |
| WO | WO 98/13361 | 4/1998 |
| WO | WO 98/56251 | 12/1998 |
| WO | WO 99/65314 | 12/1999 |
| WO | WO 99/66795 | 12/1999 |
| WO | WO 00/00029 | 1/2000 |
| WO | WO 00/00031 | 1/2000 |
| WO | WO 00/08923 | 2/2000 |
| WO | WO 00/30447 | 6/2000 |
| WO | WO 01/17350 | 3/2001 |

OTHER PUBLICATIONS

Menendez et al., "Meded—Fac. Landbouwkd. Toegepaste Biol. Wet. (Univ. Gent)", vol. 63(3a), (1998), pp. 761-767.

Pallett et al., "Extended Summary: New Perspectives in Mechanisms of Elerbicide Action," Pestic. Sci., vol. 50, (1997), pp. 83-84.

Böger, P., "Mode of Action of Herbicides Affecting Carotenogenesis,"J. Pesticide Sci., vol. 21, (1996). pp. 473-478.

Pallet et al., "Extended Summary: New Perspectives in Mechanisms of Herbicide Action", Pestic. Sci., vol. 50, pp. 83-84 (1997).

Boger et al., "Mode of Action of Herbicides Affecting Carotenogenesis", Pesticide Sci., vol. 21, pp. 473-478 (1996).

"Enhancing the margin of selectivity of RPA 201772 in *Zea mays* with Antidotes", Weed Science, vol. 47,No. 5, pp. 492-497 (1999). XP 000901419, ISSN: 0043-1745, p. 492 (abstract).

Menendez et al., Meded. Fac. Landbouwkd. Toegepaste Biol. Wet. (Univ. Gent), vol. 63(3a), pp. 761-767 (1998).

\* cited by examiner

HERBICIDE/SAFENER COMBINTIONS

The present application is a divisional of U.S. patent application Ser. No. 11/246,790 filed on Oct. 7, 2005, now abandoned which is a continuation of U.S. patent application Ser. No. 09/856,188 filed on May 17, 2001, now abandoned which claims priority from PCT Patent Application No. PCT/EP99/08470 filed on Nov. 5, 1999, which claims priority from German Patent Application No. DE 198 53 827.8 filed on Nov. 21, 1998, the disclosures of which are incorporated herein by reference in their entirety.

The invention relates to the technical field of the crop protection products, in particular the herbicide/antidote combinations (herbicide/safener combinations) which are outstandingly suitable for the use against competing harmful plants in crops of useful plants.

Some of the more recent herbicidally active substances which inhibit p-hydroxyphenylpyruvate dioxygenase (HPPDO) have very good properties on use and can be applied at very low rates against a wide spectrum of monocotyledonous and dicotyledonous weeds (see, for example, M. P. Prisbylla et al., Brighton Crop Protection Conference—Weeds (1993), 731-738).

U.S. Pat. No. 5,627,131, EP 551650 and EP 298680 disclose specific mixtures of herbicides with safeners, particularly pre-emergence safeners.

It is furthermore known from various publications that herbicides from the series of the benzoylcyclohexanediones as inhibitors of para-hydroxy-phenylpyruvate dioxygenase are based on the same mechanism of action as those from the series of the benzoylisoxazoles, cf. in this context, *J. Pesticide Sci.* 21, 473-478 (1996), *Weed Science* 45, 601-609 (1997), *Pesticide Science* 50, 83-84, (1997) and *Pesticide Outlook*, 29-32, (December 1996). Moreover, it is known from *Pesticide Science* 50, 83-84, (1997) that a benzoylisoxazole of the formula (A) can, under certain conditions, undergo rearrangement to give a benzoyl-3-oxopropionitrile of the formula (B).

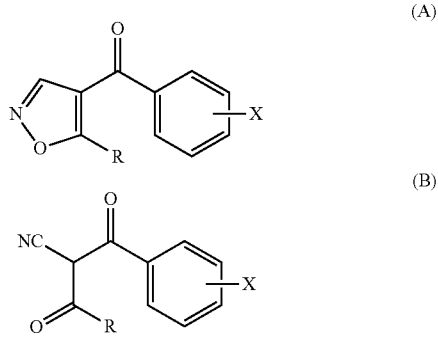

(A)

(B)

However, many of these highly effective active substances are not fully compatible with (i.e. not sufficiently selective in) some important crop plants such as maize, rice or cereals, so that their use is strictly limited. In some crops of useful plants, they can therefore only be employed in such low rates that the desired broad herbicidal activity against weeds is not guaranteed, or not at all. Specifically, a large number of the abovementioned herbicides cannot be employed fully selectively against harmful plants in maize, rice, cereals or some other crops.

To overcome these disadvantages it is known to employ herbicidally active substances in combination with a so-called safener or antidote. A safener is, for the purposes of the invention, a compound or a mixture of compounds which compensates for, or reduces, the phytotoxic properties of a herbicide toward useful plants without essentially reducing the herbicidal action against harmful plants.

Finding a safener for a particular class of herbicides remains a difficult task since the exact mechanisms by which a safener reduces the harmful action of herbicides are not known. The fact that a compound in combination with a particular herbicide acts as a safener therefore allows no conclusions as to whether such a compound would also show a safener action with other classes of herbicides. Thus, when using safeners for protecting the useful plants from adverse effects of herbicides, it has emerged that many of the safeners may still exhibit certain disadvantages. These include:

the safener reduces the action of the herbicides against the harmful plants, the useful-plant-protecting properties are not sufficient, in combination with a given herbicide, the spectrum of the useful plants in which the safener/herbicide is to be applied is not sufficiently wide, a given safener cannot always be combined with a sufficiently large number of herbicides.

It was an object of the present invention to find compounds which, in combination with the abovementioned herbicides, are suitable for increasing the selectivity of these herbicides toward important crop plants.

Surprisingly, there has now been found a group of compounds which, together with specific herbicides which act as HPPDO inhibitors increase the selectivity of these herbicides toward important crop plants.

The invention therefore relates to a herbicidally active composition comprising a mixture of A. a herbicidally active amount of one or more compounds of the formula (I)

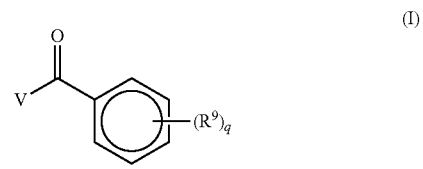

(I)

in which

V is a radical selected from the group consisting of (V1) to (V4),

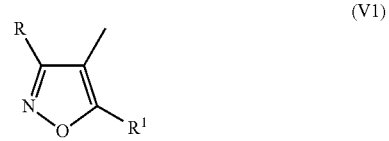

(V1)

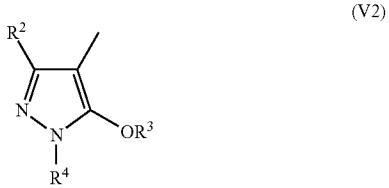

(V2)

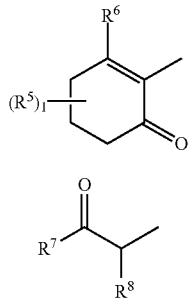

where the symbols and indices have the following meanings;
R is hydrogen, $(C_1-C_4)$-alkoxycarbonyl, $(C_1-C_4)$-haloalkoxycarbonyl, $(C_1-C_4)$-alkylsulfonyl, $(C_1-C_4)$-alkylsulfinyl, $(C_1-C_4)$-alkylthio, COOH, cyano, preferably hydrogen, $(C_1-C_4)$-alkoxycarbonyl;

$R^1$ is hydrogen, $(C_1-C_4)$-alkyl, $(C_2-C_4)$-alkenyl, $(C_2-C_4)$-alkynyl, $(C_3-C_8)$-cycloalkyl, $(C_3-C_8)$-cycloalkenyl, $(C_1-C_4)$-alkyl-$(C_3-C_8)$-cycloalkyl, $(C_3-C_7)$-halocycloalkyl, $(C_1-C_4)$-alkylthio$(C_3-C_8)$-cycloalkyl, $(C_1-C_8)$-haloalkyl or $(C_2-C_8)$-haloalkenyl, preferably $(C_3-C_7)$-cycloalkyl, $(C_1-C_4)$-alkyl-$(C_3-C_7)$-cycloalkyl;

$R^2$ is hydrogen, $(C_1-C_4)$-alkyl, $(C_1-C_4)$-alkoxy, $(C_1-C_4)$-haloalkyl, halogen, $(C_1-C_4)$-haloalkoxy, cyano, nitro, preferably hydrogen;

$R^3$ is hydrogen, $(C_1-C_4)$-alkyl, $(C_2-C_4)$-alkenyl, $(C_2-C_4)$-alkynyl, $(C_1-C_4)$-haloalkyl, $(C_1-C_4)$-alkoxy-$(C_1-C_4)$-alkyl, $(C_1-C_4)$-alkylcarbonyl, $(C_1-C_4)$-alkylsulfonyl, $(C_1-C_4)$-haloalkylsulfonyl, $(C_1-C_4)$-alkyl-substituted or unsubstituted arylsulfonyl, $(C_1-C_4)$-alkyl-substituted or unsubstituted arylcarbonyl-$(C_1-C_4)$-alkyl or $(C_1-C_4)$-alkyl-substituted or unsubstituted aryl-$(C_1-C_4)$-alkyl, preferably hydrogen, $(C_1-C_4)$-alkyl, $(C_1-C_4)$-alkyl-substituted arylsulfonyl, $(C_1-C_4)$-alkyl-arylcarbonylmethyl, benzyl;

$R^4$ is hydrogen, $(C_1-C_4)$-alkyl, $(C_2-C_4)$-alkenyl, $(C_2-C_4)$-alkynyl, $(C_1-C_4)$-haloalkyl, phenyl or benzyl, preferably $(C_1-C_4)$-alkyl;

$R^5$ is $(C_1-C_4)$-alkyl, $(C_1-C_4)$-alkoxy, $(C_1-C_4)$-alkoxy-$(C_1-C_4)$-alkyl, $(C_1-C_4)$-dialkoxy-$(C_1-C_4)$-alkyl, $(C_1-C_4)$-alkylthio, halogen, substituted or unsubstituted aryl, tetrahydropyran-4-yl, tetrahydropyran-3-yl, tetrahydrothiopyran-3-yl, 1-methylthiocyclopropyl, 2-ethylthiopropyl or two radicals $R^5$ together are $(C_2-C_4)$-alkylene, preferably $(C_1-C_4)$-alkyl, $(C_1-C_4)$-alkoxy or two radicals $R^5$ are $C_2$-alkenyl;

$R^6$ is hydroxyl, $(C_1-C_4)$-alkoxy, $(C_1-C_8)$-haloalkoxy, formyloxy, $(C_1-C_4)$-alkylcarbonyloxy, $(C_1-C_4)$-alkylsulfonyloxy, $(C_1-C_4)$-alkylthio, $(C_1-C_4)$-haloalkylthio, arylthio, aryloxy, $(C_1-C_4)$-alkylsulfinyl or $(C_1-C_4)$-alkylsulfonyl, preferably hydroxyl, $(C_1-C_4)$-alkoxy, phenylthio;

$R^7$ is $(C_1-C_4)$-alkyl, $(C_1-C_4)$-haloalkyl, $(C_3-C_8)$-cycloalkyl, $(C_1-C_4)$-alkyl-$(C_3-C_8)$-cycloalkyl or $(C_3-C_8)$-halocycloalkyl, preferably $(C_3-C_7)$-cycloalkyl;

$R^8$ is cyano, $(C_1-C_4)$-alkoxycarbonyl, $(C_1-C_4)$-alkylcarbonyl, $(C_1-C_4)$-alkylsulfonyl, $(C_1-C_4)$-alkylsulfinyl, $(C_1-C_4)$-alkylthio, $(C_1-C_4)$-alkylaminocarbonyl or $(C_1-C_4)$-dialkylaminocarbonyl, preferably cyano;

I is an integer from 0 to 6, preferably 0 to 3, where, if I≥2, the radicals $R^5$ can be identical or different from each other, and $R^9$ are identical or different nitro, amino, $(C_1-C_4)$-alkyl, $(C_2-C_4)$-alkenyl, $(C_2-C_4)$-alkynyl, halogen, $(C_1-C_4)$-haloalkyl, $(C_2-C_4)$-haloalkenyl, $(C_2-C_4)$-haloalkynyl, $(C_1-C_4)$-haloalkoxy, $(C_1-C_4)$-haloalkylthio, $(C_1-C_4)$-alkoxycarbonyl, $(C_1-C_4)$-alkylsulfonyl, $(C_1-C_4)$-alkylsulfinyl, $(C_1-C_4)$-alkylthio, arylsulfonyl, arylsulfinyl, arylthio, $(C_1-C_4)$-alkoxy, $(C_1-C_4)$-alkoxy-$(C_1-C_4)$-alkoxy, $(C_1-C_4)$-alkylthio-$(C_1-C_4)$-alkoxy, $(C_1-C_4)$-alkylcarbonyl, $(C_1-C_4)$-alkylaminosulfonyl, $(C_1-C_4)$-dialkylaminosulfonyl, $(C_1-C_4)$-alkylcarbamoyl, $(C_1-C_4)$-dialkylcarbamoyl, $(C_1-C_4)$-alkoxy-$(C_1-C_4)$-alkyl, phenoxy, cyano, aryl, alkylamino or dialkylamino, preferably $(C_1-C_4)$-alkyl, halogen, nitro, $(C_1-C_4)$-haloalkyl, $(C_1-C_4)$-haloalkoxy, $(C_1-C_4)$-alkylsulfonyl, $(C_1-C_4)$-alkylsulfonyloxy, $(C_1-C_4)$-alkylsulfonylamino, $(C_1-C_4)$-alkoxycarbonyl;

q is 0, 1, 2, 3 or 4, preferably 0, 1, 2, or 3;

and

B. an antidote-effective amount of one or more safeners selected from the group consisting of:

a) compounds of the formulae (II) to (IV),

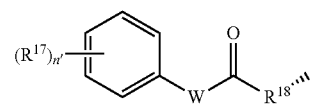

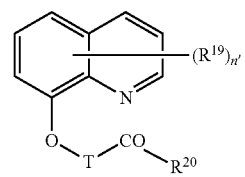

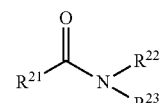

where the symbols and indices have the following meanings:

n' is a natural number from 0 to 5, preferably 0 to 3;

T is a $(C_1$ or $C_2)$-alkanediyl chain which is unsubstituted or substituted by one or two $(C_1-C_4)$-alkyl radicals or by [$(C_1-C_3)$-alkoxy]carbonyl;

W is an unsubstituted or substituted divalent heterocyclic radical selected from the group of the partially unsaturated or aromatic five-membered heterocyclic rings which have 1 to 3 hetero ring atoms of the N or O type, where the ring contains at least one N atom and not more than one O atom, preferably a radical selected from the group consisting of (W1) to (W4),

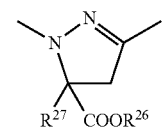

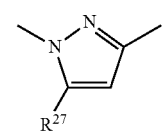

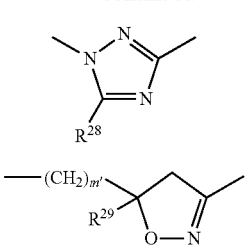

(W3)

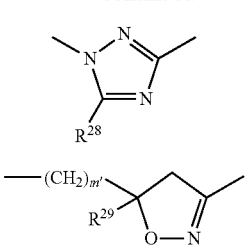

(W4)

m' is 0 or 1;

R$^{17}$, R$^{19}$ are identical or different halogen, (C$_1$-C$_4$)-alkyl, (C$_1$-C$_4$)-alkoxy, nitro or (C$_1$-C$_4$)-haloalkyl;

R$^{18}$, R$^{20}$ are identical or different OR$^{24}$, SR$^{24}$ or NR$^{24}$R$^{25}$ or a saturated or unsaturated 3- to 7-membered heterocycle having at least one N atom and up to 3 hetero atoms, preferably from the group selected from O and S, which is linked to the carbonyl group in (II) or (III) via the N atom and is unsubstituted or substituted by radicals selected from the group consisting of (C$_1$-C$_4$)-alkyl, (C$_1$-C$_4$)-alkoxy or optionally substituted phenyl, preferably a radical of the formula OR$^{24}$, NHR$^{25}$ or N(CH$_3$)$_2$, in particular of the formula OR$^{24}$;

R$^{24}$ is hydrogen or an unsubstituted or substituted aliphatic hydrocarbon radical, preferably having a total of 1 to 18 C atoms;

R$^{25}$ is hydrogen, (C$_1$-C$_6$)-alkyl, (C$_1$-C$_6$)-alkoxy or substituted or unsubstituted phenyl;

R$^{26}$ is hydrogen, (C$_1$-C$_8$)-alkyl, (C$_1$-C$_8$)-haloalkyl, (C$_1$-C$_4$)-alkoxy-(C$_1$-C$_4$)-alkyl, (C$_1$-C$_6$)-hydroxyalkyl, (C$_3$-C$_{12}$)-cycloalkyl or tri-(C$_1$-C$_4$)-alkyl-silyl;

R$^{27}$, R$^{28}$, R$^{29}$ are identical or different hydrogen, (C$_1$-C$_8$)-alkyl, (C$_1$-C$_8$)-haloalkyl, (C$_3$-C$_{12}$)-cycloalkyl or substituted or unsubstituted phenyl;

R$^{21}$ is (C$_1$-C$_4$)-alkyl, (C$_1$-C$_4$)-haloalkyl, (C$_2$-C$_4$)-alkenyl, (C$_2$-C$_4$)-haloalkenyl, (C$_3$-C$_7$)-cycloalkyl, preferably dichloromethyl;

R$^{22}$, R$^{23}$ are identical or different hydrogen, (C$_1$-C$_4$)-alkyl, (C$_2$-C$_4$)-alkenyl, (C$_2$-C$_4$)-alkynyl, (C$_1$-C$_4$)-haloalkyl, (C$_2$-C$_4$)-haloalkenyl, (C$_1$-C$_4$)-alkylcarbamoyl-(C$_1$-C$_4$)-alkyl, (C$_2$-C$_4$)-alkenylcarbamoyl-(C$_1$-C$_4$)-alkyl, (C$_1$-C$_4$)-alkoxy-(C$_1$-C$_4$)-alkyl, dioxolanyl-(C$_1$-C$_4$)-alkyl, thiazolyl, furyl, furylalkyl, thienyl, piperidyl, substituted or unsubstituted phenyl, or R$^{22}$ and R$^{23}$ together form a substituted or unsubstituted heterocyclic ring, preferably an oxazolidine, thiazolidine, piperidine, morpholine, hexahydropyrimidine or benzoxazine ring;

b) one or more compounds from the group consisting of:
1,8-naphthalic anhydride,
methyl diphenylmethoxyacetate,
cyanomethoxyimino(phenyl)acetonitrile (cyometrinil),
1,3-dioxolan-2-ylmethoxyimino(phenyl)acetonitrile (oxabetrinil),
4'-chloro-2,2,2-trifluoroacetophenone O-1,3-dioxolan-2-ylmethyloxime (fluxofenim),
4,6-dichloro-2-phenylpyrimidine (fenclorim),
benzyl 2-chloro-4-trifluoromethyl-1,3-thiazole-5-carboxylate (flurazole),
2-dichloromethyl-2-methyl-1,3-dioxolane (MG-191),
N-(4-methylphenyl)-N'-(1-methyl-1-phenylethyl)urea (dymron),
1-[4-(N-2-methoxybenzoylsulfamoyl)phenyl]-3-methylurea,
1-[4-(N-2-methoxybenzoylsulfamoyl)phenyl]-3,3-dimethylurea,
1-[4-(N-4,5-dimethylbenzoylsulfamoyl)phenyl]-3-methylurea,
1-[4-(N-naphthoylsulfamoyl)phenyl]-3,3-dimethylurea,
(2,4-dichlorophenoxy)acetic acid (2,4-D),
(4-chlorophenoxy)acetic acid,
(R,S)-2-(4-chloro-o-tolyloxy)propionic acid (mecoprop),
4-(2,4-dichlorophenoxy)butyric acid (2,4-DB),
(4-chloro-o-tolyloxy)acetic acid (MCPA),
4-(4-chloro-o-tolyloxy)butyric acid,
4-(4-chlorophenoxy)butyric acid,
3,6-dichloro-2-methoxybenzoic acid (dicamba),
1-(ethoxycarbonyl)ethyl 3,6-dichloro-2-methoxybenzoate (lactidichlor)
and their salts and esters, preferably (C$_1$-C$_8$);

c) N-acylsulfonamides of the formula (V) and their salts

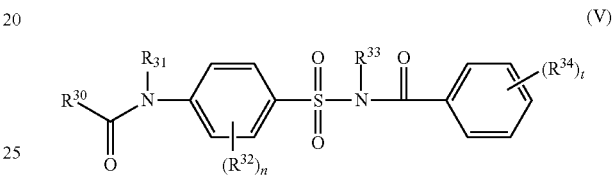

(V)

in which

R$^{30}$ is hydrogen, a hydrocarbon radical, a hydrocarbon-oxy radical, a hydrocarbon-thio radical or a heterocyclyl radical which is preferably bonded via a carbon atom, each of the 4 last-mentioned radicals being unsubstituted or being substituted by one or more identical or different radicals selected from the group consisting of halogen, cyano, nitro, amino, hydroxyl, carboxyl, formyl, carboxamide, sulfonamide and radicals of the formula Z$^a$—R$^a$, each hydrocarbon moiety preferably having 1 to 20 carbon atoms and a carbon-containing radical R$^{30}$ inclusive of substituents preferably having 1 to 30 carbon atoms;

R$^{31}$ is hydrogen or (C$_1$-C$_4$)-alkyl, preferably hydrogen, or

R$^{30}$ and R$^{31}$ together with the group of the formula —CO—N— are the residue of a 3- to 8-membered saturated or unsaturated ring;

R$^{32}$ is identical or different halogen, cyano, nitro, amino, hydroxyl, carboxyl, formyl, CONH$_2$, SO$_2$NH$_2$ or a radical of the formula Z$^b$—R$^b$;

R$^{33}$ is hydrogen or (C$_1$-C$_4$)-alkyl, preferably H;

R$^{34}$ is identical or different halogen, cyano, nitro, amino, hydroxyl, carboxyl, CHO, CONH$_2$, SO$_2$NH$_2$ or a radical of the formula Z$^c$—R$^c$, R$^a$ is a hydrocarbon radical or a heterocyclyl radical, each of the two last-mentioned radicals being unsubstituted or substituted by one or more identical or different radicals selected from the group consisting of halogen, cyano, nitro, amino, hydroxyl, mono- and di-[(C$_1$-C$_4$)-alkyl]amino, or an alkyl radical in which a plurality, preferably 2 or 3, non-adjacent CH$_2$ groups are in each case replaced by one oxygen atom;

R$^b$,R$^c$ are identical or different and are a hydrocarbon radical or a heterocyclyl radical, each of the two last-mentioned radicals being unsubstituted or substituted by one or more identical or different radicals selected from the group consisting of halogen, cyano, nitro, amino, hydroxyl, phosphoryl, halo-(C$_1$-C$_4$)-alkoxy, mono- and di-[(C$_1$-C$_4$)-alkyl] amino, or an alkyl radical in which a plurality, preferably 2 or 3, non-adjacent CH$_2$ groups are replaced in each case by one oxygen atom;

$Z^a$ is a divalent group of the formula O, S, CO, CS, CO—O, CO—S, O—CO, S—CO, SO, SO$_2$, NR*, CO—NR*, NR*—CO, SO$_2$—NR* or NR*—SO$_2$, the bond given on the right-hand side of each of the divalent groups being the bond to the radical $R^a$, and the radicals R* in the 5 last-mentioned radicals independently of each other being in each case H, (C$_1$-C$_4$)-alkyl or halo-(C$_1$-C$_4$)-alkyl;

$Z^b, Z^c$ independently of one another are a direct bond or a divalent group of the formula O, S, CO, CS, CO—O, CO—S, O—CO, S—CO, SO, SO$_2$, NR*, SO$_2$—NR*, NR*—SO$_2$, CO—NR* or NR*—CO, where, in asymmetrical divalent groups, the atom on the right-hand side is linked to the radical $R^b$ or $R^c$ and where the radicals R* in the 5 last-mentioned radicals independently of one another are in each case H, (C$_1$-C$_4$)-alkyl or halo-(C$_1$-C$_4$)-alkyl;

n is an integer from 0 to 4, preferably 0, 1 or 2, in particular 0 or 1, and t is an integer from 0 to 5, preferably 0, 1, 2 or 3, in particular 0, 1 or 2;

d) acylsulfamoylbenzamides of the formula (VI), optionally also in salt form,

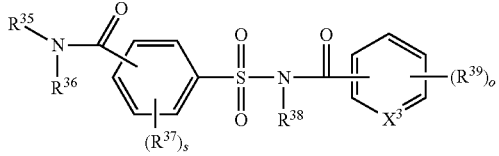

(VI)

in which $X^3$ is CH or N;

$R^{35}$ is hydrogen, heterocyclyl or a hydrocarbon radical, the two last-mentioned radicals optionally being substituted by one or more identical or different radicals selected from the group consisting of halogen, cyano, nitro, amino, hydroxyl, carboxyl, CHO, CONH$_2$, SO$_2$NH$_2$ and $Z^d$—$R^d$;

$R^{36}$ is hydrogen, hydroxyl, (C$_1$-C$_6$)-alkyl, (C$_2$-C$_6$)-alkenyl, (C$_2$-C$_6$)-alkynyl, (C$_1$-C$_6$)-alkoxy, (C$_2$-C$_6$)-alkenyloxy, the five last-mentioned radicals optionally being substituted by one or more identical or different radicals selected from the group consisting of halogen, hydroxyl, (C$_1$-C$_4$)-alkyl, (C$_1$-C$_4$)-alkoxy and (C$_1$-C$_4$)-alkylthio, or $R^{35}$ and $R^{36}$ together with the nitrogen atom to which they are attached are a 3- to 8-membered saturated or unsaturated ring;

$R^{37}$ is identical or different halogen, cyano, nitro, amino, hydroxyl, carboxyl, CHO, CONH$_2$, SO$_2$NH$_2$ or $Z^e$—$R^e$;

$R^{38}$ is hydrogen, (C$_1$-C$_4$)-alkyl, (C$_2$-C$_4$)-alkenyl or (C$_2$-C$_4$)-alkynyl;

$R^{39}$ is identical or different halogen, cyano, nitro, amino, hydroxyl, carboxyl, phosphoryl, CHO, CONH$_2$, SO$_2$NH$_2$ or $Z^f$—$R^f$;

$R^d$ is a (C$_2$-C$_{20}$)-alkyl radical whose carbon chain is interrupted once or more than once by oxygen atoms, or is heterocyclyl or a hydrocarbon radical, the two last-mentioned radicals optionally being substituted by one or more identical or different radicals selected from the group consisting of halogen, cyano, nitro, amino, hydroxyl, mono- and di-[(C$_1$-C$_4$)-alkyl]amino;

$R^e$, $R^f$ are identical or different and are a (C$_2$-C$_{20}$)-alkyl radical whose carbon chain is interrupted once or more than once by oxygen atoms, or a heterocyclyl or a hydrocarbon radical, the two last-mentioned radicals optionally being substituted by one or more identical or different radicals selected from the group consisting of halogen, cyano, nitro, amino, hydroxyl, phosphoryl, (C$_1$-C$_4$)-haloalkoxy, mono- and di-[(C$_1$-C$_4$)-alkyl]amino;

$Z^d$ is a divalent unit selected from the group consisting of O, S, CO, CS, C(O)O, C(O)S, SO, SO$_2$, NR*, C(O)NR* or SO$_2$NR*;

$Z^e$, $Z^f$ are identical or different and are a direct bond or a divalent unit selected from the group consisting of O, S, CO, CS, C(O)O, C(O)S, SO, SO$_2$, NR*, SO$_2$NR* or C(O)NR*;

R* is hydrogen, (C$_1$-C$_4$)-alkyl or (C$_1$-C$_4$)-haloalkyl;

s is an integer from 0 to 4, and o in the event that X is CH, is an integer from 0 to 5 and, in the event that X is N, is an integer from 0 to 4;

e) compounds of the formula (VII),

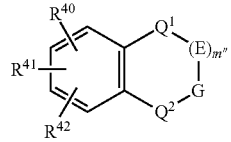

(VII)

in which the symbols and indices have the following meanings:

$R^{40}$ is H, (C$_1$-C$_4$)-alkyl, (C$_1$-C$_4$)-alkyl substituted by (C$_1$-C$_4$)-alkyl-X$^4$ or (C$_1$-C$_4$)-haloalkyl-X$^4$, (C$_1$-C$_4$)-haloalkyl, NO$_2$, CN, —COO—$R^{43}$, NR$_2^{44}$, SO$_2$NR$_2^{45}$ or CONR$_2^{46}$;

$R^{41}$ is H, halogen, (C$_1$-C$_4$)-alkyl, CF$_3$, (C$_1$-C$_4$)-alkoxy or (C$_1$-C$_4$)-haloalkoxy;

$R^{42}$ is H, halogen or (C$_1$-C$_4$)-alkyl;

$Q^1$, $Q^2$, E, G are identical or different, O, S, CR$_2^{47}$, CO, NR$^{48}$ or a group of the formula (VIII),

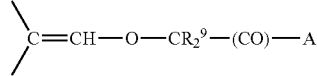

(VIII)

with the proviso that

α) at least one of the groups $Q^1$, $Q^2$, E, G is a carbonyl group, that exactly one of these groups is a radical of the formula (VIII) and that the group of the formula (VIII) is adjacent to a carbonyl group, and β) two adjacent groups $Q^1$, $Q^2$, E and G cannot simultaneously be oxygen;

$R^g$ is identical or different H or (C$_1$-C$_8$)-alkyl or the two radicals $R^g$ together are (C$_2$-C$_6$)-alkylene;

A is Y$^3$—$R^h$ or NR$_2^{49}$;

$X^4$ is O or S(O)$_x$;

$Y^3$ is O or S;

$R^h$ is H, (C$_1$-C$_8$)-alkyl, (C$_1$-C$_8$)-haloalkyl, (C$_1$-C$_4$)-alkoxy-(C$_1$-C$_8$)-alkyl, (C$_3$-C$_6$)-alkenyloxy-(C$_1$-C$_8$)-alkyl, or phenyl-(C$_1$-C$_8$)-alkyl, where the phenyl ring is optionally substituted by halogen, (C$_1$-C$_4$)-alkyl, CF$_3$, methoxy or methyl-S(O)$_x$; (C$_3$-C$_6$)alkenyl, (C$_3$-C$_6$)-haloalkenyl, phenyl-(C$_3$-C$_6$)-alkenyl, (C$_3$-C$_6$)-alkynyl, phenyl-(C$_3$-C$_6$)-alkynyl, oxetanyl, furfuryl, tetrahydrofuryl;

$R^{43}$ is H or (C$_1$-C$_4$)-alkyl;

$R^{44}$ is identical or different H, (C$_1$-C$_4$)-alkyl, (C$_1$-C$_4$)-alkylcarbonyl or the two radicals $R^{44}$ together are (C$_4$-C$_5$)-alkylene;

$R^{45}$, $R^{46}$ independently of one another are in each case identical or different H, (C$_1$-C$_4$)-alkyl, or the two radicals $R^{45}$ and/or $R^{46}$ together are $(C_4-C_5)$-alkylene, where one $CH_2$ group can be replaced by O or S or one or two $CH_2$ groups can be replaced by $NR^i$;

$R^i$ is H or $(C_1-C_8)$-alkyl;

$R^{47}$ is identical or different H, $(C_1-C_8)$-alkyl or the two radicals $R^{47}$ together are $(C_2-C_6)$-alkylene;

$R^{48}$ is H, $(C_1-C_8)$-alkyl, substituted or unsubstituted phenyl, or benzyl which is unsubstituted or substituted on the phenyl ring;

$R^{49}$ is identical or different H, $(C_1-C_8)$-alkyl, phenyl, phenyl-$(C_1-C_8)$-alkyl, where a phenyl ring can be substituted by F, Cl, Br, $NO_2$, CN, $OCH_3$, $(C_1-C_4)$-alkyl or $CH_3SO_2$-; $(C_1-C_4)$-alkoxy-$(C_1-C_8)$-alkyl, $(C_3-C_6)$-alkenyl, $(C_3-C_6)$-alkynyl, $(C_3-C_6)$-cycloalkyl or two radicals $R^{49}$ together are $(C_4-C_5)$-alkylene, where one $CH_2$ group can be replaced by O or S or one or two $CH_2$ groups can be replaced by $NR^k$;

$R^k$ is H or $(C_1-C_4)$-alkyl;

m" is 0 or 1 and x is 0, 1 or 2;

inclusive of the stereoisomers and the agriculturally customary salts, with the exclusion of mixtures in which a) in the compound of the formula (I), V=V1 or V4 and the safener has the formula (IV) or is selected from the group consisting of 1,8-naphthalic anhydride; methyldiphenylmethoxyacetate; 2-dichloro-methyl-2-methyl-1,3-dioxolane; cyanomethoxyimino(phenyl)acetonitrile; 1,3-dioxolan-2-ylmethoxyimino(phenyl)acetonitrile; 4'-chloro-2,2,2-trifluoroacetophenone O-1,3-dioxolan-2-ylmethyloxime; 4,6-dichloro-2-phenylpyrimidine; benzyl-2-chloro-4-trifluormethyl-1,3-thiazole-5-carboxylate and 1-methylhexyl(5-chloro-8-quinolinoxy)acetate; or b) in the compound of the formula (I), V=V3 where $R^6$=OH, and the safener has the formula (II) where W=W1, W2, W3 or W4 where m'=1 or has the formula (III) and T is a $(C_1$- or $C_2)$-alkanediyl chain which is unsubstituted or substituted by one or two $(C_1-C_4)$-alkyl radicals, or has the formula (IV), or is a compound from the group consisting of 1,8-naphthalic anhydride, oxabetrinil, cyanomethoxyimino(phenyl)acetonitrile, fluxofenim and flurazole.

A herbicidally active amount is, for the purposes of the invention, such an amount of one or more herbicides which is capable of adversely affecting plant growth.

An antidotically effective amount is, for the purposes of the invention, such an amount of one or more safeners which is capable of at least partially countering the phytotoxic effect of a herbicide or herbicide mixture on a useful plant.

Unless otherwise defined individually, the following definitions generally apply to the radicals in the formulae (I) to (VIII) and in the subsequent formulae.

The radicals alkyl, alkoxy, haloalkyl, haloalkoxy, alkylamino and alkylthio and the corresponding unsaturated and/or substituted radicals can be in each case straight-chain or branched in the carbon skeleton. Alkyl radicals, also the composite meanings such as alkoxy, haloalkyl and the like, preferably have 1 to 4 carbon atoms and are, for example, methyl, ethyl, n- or i-propyl or n-, i-, t- or 2-butyl. Alkenyl and alkynyl radicals have the meanings of the unsaturated radicals which are possible which correspond to the alkyl radicals; alkenyl is, for example, allyl, 1-methylprop-2-en-1-yl, 2-methylprop-2-en-1-yl, but-2-en-1-yl, but-3-en-1-yl, 1-methylbut-3-en-1-yl and 1-methylbut-2-en-1-yl. Alkynyl is, for example, propargyl, but-2-yn-1-yl, but-3-yn-1-yl, 1-methylbut-3-yn-1-yl. "$(C_1-C_4)$-Alkyl" is the abbreviation for alkyl having 1 to 4 carbon atoms; the same applies analogously to other general definitions of radicals, where the range of the possible number of carbon atoms is indicated in brackets.

Cycloalkyl is, preferably, a cyclic alkyl radical having 3 to 8, preferably 3 to 7, especially preferably 3 to 6, carbon atoms, for example cyclopropyl, cyclobutyl, cyclopentyl and cyclohexyl. Cycloalkenyl and cycloalkinyl denote corresponding unsaturated compounds.

Halogen is fluorine, chlorine, bromine or iodine. Haloalkyl, haloalkenyl and haloalkynyl are alkyl, alkenyl or alkynyl which are partially or fully substituted by halogen, preferably by fluorine, chlorine and/or bromine, in particular by fluorine or chlorine, for example $CF_3$, $CHF_2$, $CH_2F$, $CF_3CF_2$, $CH_2FCHCl$, $CCl_3$, $CHCl_2$, $CH_2CH_2Cl$. Haloalkoxy is, for example, $OCF_3$, $OCHF_2$, $OCH_2F$, $CF_3CF_2O$, $OCH_2CF_3$ and $OCH_2CH_2Cl$. This also applies analogously to other halogen-substituted radicals.

A hydrocarbon radical can be an aromatic or an aliphatic hydrocarbon radical, where an aliphatic hydrocarbon radical is generally a straight-chain or branched saturated or unsaturated hydrocarbon radical, preferably having 1 to 18, especially preferably 1 to 12, carbon atoms, for example alkyl, alkenyl or alkynyl.

Aliphatic hydrocarbon radical preferably means alkyl, alkenyl or alkynyl having up to 12 carbon atoms; the same applies analogously to an aliphatic hydrocarbon radical in a hydrocarbon-oxy radical.

Aryl is generally a mono-, bi- or polycyclic aromatic system having by preference 6-20 carbon atoms, preferably 6 to 14 carbon atoms, especially preferably 6 to 10 carbon atoms, for example phenyl, naphthyl, tetrahydronaphthyl, indenyl, indanyl, pentalenyl and fluorenyl, especially preferably phenyl.

Heterocyclic ring, heterocyclic radical or heterocyclyl is a mono-, bi- or polycyclic ring system which is saturated, unsaturated and/or aromatic and contains one or more, preferably 1 to 4, hetero atoms, preferably selected from the group consisting of N, S and O.

Preferred are saturated heterocycles having 3 to 7 ring atoms and one or two hetero atoms selected from the group consisting of N, O and S, their chalcogens not being adjacent. Especially preferred are monocyclic rings having 3 to 7 ring atoms and a hetero atom selected from the group consisting of N, O and S, and also morpholine, dioxolane, piperazine, imidazoline and oxazolidine. Very especially preferred saturated heterocycles are oxirane, pyrrolidone, morpholine and tetrahydrofuran.

Also preferred are partially unsaturated heterocycles having 5 to 7 ring atoms and one or two hetero atoms selected from the group consisting of N, O and S. Especially preferred are partially unsaturated heterocycles having 5 to 6 ring atoms and one hetero atom selected from the group consisting of N, O and S. Very especially preferred partially unsaturated heterocycles are pyrazoline, imidazoline and isoxazoline.

Equally preferred is heteroaryl; for example mono- or bicyclic aromatic heterocycles having 5 to 6 ring atoms which contain one to four hetero atoms selected from the group consisting of N, O, S, the chalcogens not being adjacent. Especially preferred are monocyclic aromatic heterocycles having 5 to 6 ring atoms which contains a hetero atom selected from the group consisting of N, O and S, and also pyrimidine, pyrazine, pyridazine, oxazole, thiazole, thiadiazole, oxadiazole, pyrazole, triazole and isoxazole. Very especially preferred are pyrazole, thiazole, triazole and furan.

Substituted radicals, such as substituted hydrocarbon radicals, for example substituted alkyl, alkenyl, alkynyl, aryl such as phenyl and arylalkyl such as benzyl, or substituted heterocyclyl, are a substituted radical which is derived from an unsubstituted skeleton, the substituents being, by preference, one or more, by preference 1, 2 or 3, in the case of Cl and F also up to the maximum possible number of, substituents selected from the group consisting of halogen, alkoxy, haloalkoxy, alkylthio, hydroxyl, amino, nitro, carboxyl, cyano, azido, alkoxycarbonyl, alkylcarbonyl, formyl, carbamoyl, mono- and dialkylaminocarbonyl, substituted amino such as acylamino, mono- and dialkylamino and alkylsulfynyl, haloalkylsulfynyl, alkylsulfonyl, haloalkylsulfonyl and, in the case of cyclic radicals, also alkyl and haloalkyl and the unsaturated aliphatic substituents which correspond to the abovementioned saturated hydrocarbon-containing substituents, preferably alkenyl, alkynyl, alkenyloxy and alkynyloxy. In the case of radicals having carbon atoms, those having 1 to 4 carbon atoms, in particular 1 or 2 carbon atoms, are preferred. As a rule, preferred substituents are those selected from the group consisting of halogen, for example fluorine or chlorine, ($C_1$-$C_4$)-alkyl, preferably methyl or ethyl, ($C_1$-$C_4$)-haloalkyl, preferably trifluoromethyl, ($C_1$-$C_4$)-alkoxy, preferably methoxy or ethoxy, ($C_1$-$C_4$)-haloalkoxy, nitro and cyano. Especially preferred in this context are the substituents methyl, methoxy and chlorine.

Mono- or disubstituted amino is a chemically stable radical selected from the group of the substituted amino radicals which are N-substituted by, for example, one or two identical or different radicals selected from the group consisting of alkyl, alkoxy, acyl and aryl; preferably monoalkylamino, dialkylamino, acylamino, arylamino, N-alkyl-N-Arylamino and N-heterocycles. Preferred in this context are alkyl radicals having 1 to 4 carbon atoms. By preference, aryl is phenyl. By preference, substituted aryl is substituted phenyl. The definition given further below applies to acyl, preferably ($C_1$-$C_4$)-alkanoyl. This also applies analogously to substituted hydroxylamino or hydrazino.

By preference, optionally substituted phenyl is phenyl which is unsubstituted or mono- or polysubstituted, preferably up to trisubstituted, in the case of halogen such as Cl and F also up to pentasubstituted, by identical or different radicals selected from the group consisting of halogen, ($C_1$-$C_4$)-alkyl, ($C_1$-$C_4$)-alkoxy, ($C_1$-$C_4$)-haloalkyl, ($C_1$-$C_4$)-haloalkoxy and nitro, for example o-, m- and p-tolyl, dimethylphenyls, 2-, 3- and 4-chloro-phenyl, 2-, 3- and 4-trifluoro- and -trichlorophenyl, 2,4-, 3,5-, 2,5- and 2,3-dichlorophenyl, o-, m- and p-methoxyphenyl.

An acyl radical is the radical of an organic acid having by preference up to 6 carbon atoms, for example the radical of a carboxylic acid and radicals of acids derived therefrom, such as thiocarboxylic acid, optionally N-substituted iminocarboxylic acids, or the radical of carbonic monoesters, optionally N-substituted carbamic acids, sulfonic acid, sulfinic acids, phoshonic acids, phosphinic acids. Acyl is, for example, formyl, alkylcarbonyl such as ($C_1$-$C_4$-alkyl)-carbonyl, phenylcarbonyl, it being possible for the phenyl ring to be substituted, for example as indicated above for phenyl, or alkyloxycarbonyl, phenyloxycarbonyl, benzyloxycarbonyl, alkylsulfonyl, alkylsulfynyl or N-alkyl-1-iminoalkyl.

All stereoisomers which show the same topological linkage of the atoms, and their mixtures, also fall under the formulae (I) to (VIII). Such compounds contain one or more asymmetric carbon atoms or else double bonds which are not indicated specifically in the general formulae. The stereoisomers which are possible which are defined by their specific spatial form, such as enantiomers, diastereomers, Z- and E-isomers, can be obtained form mixtures of the stereoisomers by customnary methods or else be prepared by stereoselective reactions in combination with the use of stereochemically pure starting materials.

Herbicidally active substances which are suitable in accordance with the invention are those compounds of the formula (I) which, on their own, cannot be used, or not optimally used, in cereal crops, rice and/or maize because they are too harmful to the crop plants.

Herbicides of the formula (I) are known, for example, from EP-A 0 137 963, EP-A 0 352 543, EP-A 0 418 175, EP-A 0 496 631 and AU-A 672 058. The compounds of the formula (II) are known, for example, from EP-A-0 333 131 (ZA-89/1960), EP-A-0 269 806 (U.S. Pat. No. 4,891,057), EP-A-0 346 620 (AU-A-89/34951), EP-A-0 174 562, EP-A-0 346 620 (WO-A-91/08 202), WO-A-91/07 874 or WO-A 95/07 897 (ZA 94/7120) and the literature cited therein or can be prepared by or analogously to the processes described therein. The compounds of the formula (III) are known from EP-A-0 086 750, EP-A-0 94349 (U.S. Pat. No. 4,902,340), EP-A-0 191736 (U.S. Pat. No. 4,881,966) and EP-A-0 492 366 and the literature cited therein or can be prepared by or analogously to the processes described therein. Furthermore, some compounds are described in EP-A-0 582 198. The compounds of the formula (IV) are known from a large number of patent applications, for example U.S. Pat. Nos. 4,021,224 and 4,021,229. Moreover, compounds from group (b) are known from CN-A-87/102 789, EP-A-365484 and from "The Pesticide Manual", The British Crop Protection Council and the Royal Society of Chemistry, 11th edition, Farnham 1997. The compounds of group (c) are described in WO-A-97/45016, those of group (d) in German Patent Application 197 42 951.3 and those of group (e) in WO-A 98/13 361. The publications cited contain detailed information on preparation processes and starting materials. These publications are incorporated herein by reference.

Preferred herbicide/safener combinations are those which comprise safeners of the formula (II) and/or (III) where the symbols and indices have the following meanings:

$R^{24}$ is hydrogen, ($C_1$-$C_{18}$)-alkyl, ($C_3$-$C_{12}$)-cycloalkyl, ($C_2$-$C_8$)-alkenyl and ($C_2$-$C_{18}$)-alkynyl, where the carbon-containing groups can be substituted by one or more preferably up to three, radicals $R^{50}$;

$R^{50}$ is identical or different halogen, hydroxyl, ($C_1$-$C_8$)-alkoxy, ($C_1$-$C_8$)-alkylthio, ($C_2$-$C_8$)-alkenylthio, ($C_2$-$C_8$)-alkynylthio, ($C_2$-$C_8$)-alkenyloxy, ($C_2$-$C_8$)-alkynyloxy, ($C_3$-$C_7$)-cycloalkyl, ($C_3$-$C_7$)-cycloalkoxy, cyano, mono- and di-($C_1$-$C_4$)-alkyl)amino, carboxyl, ($C_1$-$C_8$)-alkoxycarbonyl, ($C_2$-$C_8$)-alkenyloxycarbonyl, ($C_1$-$C_8$)-alkylthiocarbonyl, ($C_2$-$C_8$)-alkynyloxycarbonyl, ($C_1$-$C_8$)-alkylcarbonyl, ($C_2$-$C_8$)-alkenylcarbonyl, ($C_2$-$C_8$)-alkynylcarbonyl, 1-(hydroxyimino)-($C_1$-$C_6$)-alkyl, 1-[($C_1$-$C_4$)-alkylimino]-($C_1$-$C_4$)-alkyl, 1-[($C_1$-$C_4$)-alkoxyimino]-($C_1$-$C_6$)-alkyl, ($C_1$-$C_8$)-alkylcarbonylamino, ($C_2$-$C_8$)-alkenylcarbonylamino, ($C_2$-$C_8$)-alkynylcarbonylamino, aminocarbonyl, ($C_1$-$C_8$)-alkylaminocarbonyl, di-($C_1$-$C_6$)-alkylaminocarbonyl, ($C_2$-$C_6$)-alkenylaminocarbonyl, ($C_2$-$C_6$)-alkynylaminocarbonyl, ($C_1$-$C_8$)-alkoxycarbonylamino, ($C_1$-$C_8$)-alkylaminocarbonylamino, ($C_1$-$C_6$)-alkylcarbonyloxy which is unsubstituted or substituted by $R^{51}$, or is ($C_2$-$C_6$)-alkenylcarbonyloxy, ($C_2$-$C_6$)-alkynylcarbonyloxy, ($C_1$-$C_8$)-alkylsulfonyl, phenyl, phenyl-($C_1$-$C_6$)-alkoxy, phenyl-($C_1$-$C_6$)-alkoxycarbonyl, phenoxy, phenoxy-($C_1$-$C_6$)-alkoxy, phenoxy-($C_1$-$C_6$)-alkoxycarbonyl, phenylcarbonyloxy, phenylcarbonylamino, phenyl-($C_1$-$C_6$)-alkylcarbonylamino, it being possible for the last-mentioned 9 radicals to be unsubstituted or mono- or polysubstituted, preferably up to trisubstituted, by radicals $R^{52}$; SiR'$_3$, OSiR'$_3$, R'$_3$Si—($C_1$-$C_8$)-alkoxy, CO—O—

NR'$_2$, O—N=CR'$_2$, N=CR'$_2$, O—NR'$_2$, NR'$_2$, CH(OR')$_2$, O—(CH$_2$)$_q$—CH(OR')$_2$, CR'''(OR')$_2$, O—(CH$_2$)$_w$CR''' (OR'')$_2$ or by R''O—CHR'''CHCOR''—(C$_1$-C$_6$)-alkoxy, $R^{51}$ is identical or different halogen, nitro, (C$_1$-C$_4$)-alkoxy and phenyl which is unsubstituted or substituted by one or more, preferably up to three, radicals $R^{52}$;

$R^{52}$ is identical or different halogen, (C$_1$-C$_4$)-alkyl, (C$_1$-C$_4$)-alkoxy, (C$_1$-C$_4$)-haloalkyl, (C$_1$-C$_4$)-haloalkoxy or nitro;

R' is identical or different hydrogen, (C$_1$-C$_4$)-alkyl, phenyl which is unsubstituted or substituted by one or more, preferably up to three, radicals $R^{52}$, or two radicals R' together form a (C$_2$-C$_6$)-alkanediyl chain;

R'' is identical or different (C$_1$-C$_4$)-alkyl or two radicals R'' together form a (C$_2$-C$_6$)-alkanediyl chain;

R''' is hydrogen or (C$_1$-C$_4$)-alkyl;

w is 0, 1, 2, 3, 4, 5 or 6.

Especially preferred are herbicide/safener combinations according to the invention which comprise safeners of the formula (II) and/or (III) where the symbols and indices have the following meanings:

$R^{24}$ is hydrogen, (C$_1$-C$_8$)-alkyl or (C$_3$-C$_7$)-cycloalkyl, the above carbon-containing radicals being unsubstituted or mono- or polysubstituted by halogen or mono- or disubstituted, by preference monosubstituted, by radicals $R^{50}$, $R^{50}$ is identical or different hydroxyl, (C$_1$-C$_4$)-alkoxy, carboxyl, (C$_1$-C$_4$)-alkoxycarbonyl, (C$_2$-C$_6$)-alkenyloxycarbonyl, (C$_2$-C$_6$)-alkynyloxycarbonyl, 1-(hydroxyimino)-(C$_1$-C$_4$)-alkyl, 1-[(C$_1$-C$_4$)-alkylimino]-(C$_1$-C$_4$)-alkyl and 1-[(C$_1$-C$_4$)-alkoxyimino]-(C$_1$-C$_4$)-alkyl; SiR'$_3$, O—N=CR'$_2$, N=CR'$_2$, NR'$_2$ and ONR'$_3$ where R' is identical or different hydrogen, (C$_1$-C$_4$)-alkyl or, as a pair, a (C$_4$-C$_5$)-alkanediyl chain, $R^{27}$, $R^{28}$, $R^{29}$ are identical or different hydrogen, (C$_1$-C$_8$)-alkyl, (C$_1$-C$_6$)-haloalkyl, (C$_3$-C$_7$)-cycloalkyl or phenyl which is unsubstituted or substituted by one or more radicals selected from the group consisting of halogen, cyano, nitro, amino, mono- and di-[(C$_1$-C$_4$)-alkyl]-amino, (C$_1$-C$_4$)-alkyl, (C$_1$-C$_4$)-haloalkyl, (C$_1$-C$_4$)-alkoxy, (C$_1$-C$_4$)-haloalkoxy, (C$_1$-C$_4$)-alkylthio and (C$_1$-C$_4$)-alkylsulfonyl;

$R^{26}$ is hydrogen, (C$_1$-C$_8$)-alkyl, (C$_1$-C$_8$)-haloalkyl, (C$_1$-C$_4$)-alkoxy)-(C$_1$-C$_4$)-alkyl, (C$_1$-C$_6$)-hydroxyalkyl, (C$_3$-C$_7$)-cycloalkyl or tri-(C$_1$-C$_4$)-alkylsilyl, $R^{17}$, $R^{19}$ are identical or different halogen, methyl, ethyl, methoxy, ethoxy, (C$_1$ or C$_2$)-haloalkyl, by preference hydrogen, halogen or (C$_1$ or C$_2$)-haloalkyl.

Very especially preferred are safeners in which the symbols and indices in formula (II) have the following meanings:

$R^{17}$ is halogen, nitro or (C$_1$-C$_4$)-haloalkyl;

n' is 0, 1, 2 or 3;

$R^{18}$ is a radical of the formula OR$^{24}$, $R^{24}$ is hydrogen, (C$_1$-C$_8$)-alkyl or (C$_3$-C$_7$)-cycloalkyl, where the above carbon-containing radicals are unsubstituted or mono- or polysubstituted, by preference up to trisubstituted, by identical or difference halogen radicals or up to disubsubstituted, by preference monosubstituted, by identical or different radicals selected from the group consisting of hydroxyl, (C$_1$-C$_4$)-alkoxy, (C$_1$-C$_4$)-alkoxycarbonyl, (C$_2$-C$_6$)-alkenyloxycarbonyl, (C$_2$-C$_6$)-alkynyloxycarbonyl, 1-(hydroxyimino)-(C$_1$-C$_4$)-alkyl, 1-[(C$_1$-C$_4$)-alkylimino]-(C$_1$-C$_4$)-alkyl, 1-[(C$_1$-C$_4$)-alkoxyimino]-(C$_1$-C$_4$)-alkyl and radicals of the formulae SiR'$_3$, O—N=CR'$_2$, N=CR'$_2$, NR'$_2$ and O—NR'$_2$, where the radicals R' in the abovementioned formulae are identical or different hydrogen, (C$_1$-C$_4$)-alkyl or, as a pair, are (C$_4$ or C$_5$)-alkanediyl;

$R^{27}$, $R^{28}$, $R^{29}$ are identical or different hydrogen, (C$_1$-C$_8$)-alkyl, (C$_1$-C$_6$)-haloalkyl, (C$_3$-C$_7$)-cycloalkyl or phenyl which is unsubstituted or substituted by one or more radicals selected from the group consisting of halogen, (C$_1$-C$_4$)-alkyl, (C$_1$-C$_4$)-alkoxy, nitro, (C$_1$-C$_4$)-haloalkyl and (C$_1$-C$_4$)-haloalkoxy, and $R^{26}$ is hydrogen, (C$_1$-C$_8$)-alkyl, (C$_1$-C$_8$)-haloalkyl, (C$_1$-C$_4$)-alkoxy-(C$_1$-C$_4$)-alkyl, (C$_1$-C$_6$)-hydroxyalkyl, (C$_3$-C$_7$)-cycloalkyl or tri-(C$_1$-C$_4$)-alkylsilyl.

Very especially preferred are also safeners of the formula (III) where the symbols and indices have the following meanings:

$R^{19}$ is halogen or (C$_1$-C$_4$)-haloalkyl;

n' is 0, 1, 2 or 3, where (R$^{19}$)$_{n'}$ is, by preference, 5-Cl;

$R^{20}$ is a radical of the formula OR$^{24}$;

T is CH$_2$ or CH(COO—(C$_1$-C$_3$)-alkyl) and $R^{24}$ is hydrogen, (C$_1$-C$_8$)-alkyl, (C$_1$-C$_8$)-haloalkyl or (C$_1$-C$_4$)-alkoxy-(C$_1$-C$_4$)-alkyl, by preference (C$_1$-C$_8$)-alkyl.

Especially preferred are safeners of the formula (II) where the symbols and indices have the following meanings:

W is (W1);

$R^{17}$ is halogen or (C$_1$-C$_2$)-haloalkyl;

n' is 0, 1, 2 or 3, where (R$^{17}$)$_{n'}$ is by preference 2,4-Cl$_2$;

$R^{18}$ is a radical of the formula OR$^{24}$;

$R^{24}$ is hydrogen, (C$_1$-C$_8$)-alkyl, (C$_1$-C$_4$)-haloalkyl, (C$_1$-C$_4$)-hydroxyalkyl, (C$_3$-C$_7$)-cycloalkyl, (C$_1$-C$_4$)-alkoxy-(C$_1$-C$_4$)-alkyl or tri-(C$_1$-C$_2$)-alkylsilyl, by preference (C$_1$-C$_4$)-alkyl;

$R^{27}$ is hydrogen, (C$_1$-C$_8$)-alkyl, (C$_1$-C$_4$)-haloalkyl or (C$_3$-C$_7$)-cycloalkyl, by preference hydrogen or (C$_1$-C$_4$)-alkyl, and $R^{26}$ is hydrogen, (C$_1$-C$_8$)-alkyl, (C$_1$-C$_4$)-haloalkyl, (C$_1$-C$_4$)-hydroxyalkyl, (C$_3$-C$_7$)-cycloalkyl, (C$_1$-C$_4$)-alkoxy-(C$_1$-C$_4$)-alkyl or tri-(C$_1$-C$_2$)-alkylsilyl, by preference hydrogen or (C$_1$-C$_4$)-alkyl.

Also especially preferred are herbicidal compositions comprising a safener of the formula (II) where the symbols and indices have the following meanings:

W is (W2);

$R^{17}$ is halogen or (C$_1$-C$_2$)-haloalkyl;

n' is 0, 1, 2 or 3, where (R$^{17}$)$_{n'}$ is by preference 2,4-Cl$_2$;

$R^{18}$ is a radical of the formula OR$^{24}$;

$R^{24}$ is hydrogen, (C$_1$-C$_8$)-alkyl, (C$_1$-C$_4$)-haloalkyl, (C$_1$-C$_4$)-hydroxyalkyl, (C$_3$-C$_7$)-cycloalkyl, (C$_1$-C$_4$-alkoxy)-(C$_1$-C$_4$)-alkyl or tri-(C$_1$-C$_2$)-alkyl-silyl, by preference (C$_1$-C$_4$)-alkyl, and $R^{27}$ is hydrogen, (C$_1$-C$_8$)-alkyl, (C$_1$-C$_4$)-haloalkyl, (C$_3$-C$_7$)-cycloalkyl or phenyl, by preference hydrogen or (C$_1$-C$_4$)-alkyl.

Also especially preferred are safeners of the formula (II) where the symbols and indices have the following meanings:

W is (W3);

$R^{17}$ is halogen or (C$_1$-C$_2$)-haloalkyl;

n' is 0, 1, 2 or 3, where (R$^{17}$)$_{n'}$ by preference 2,4-Cl$_2$;

$R^{18}$ is a radical of the formula OR$^{24}$;

$R^{24}$ is hydrogen, (C$_1$-C$_8$)-alkyl, (C$_1$-C$_4$)-haloalkyl, (C$_1$-C$_4$)-hydroxyalkyl, (C$_3$-C$_7$)-cycloalkyl, (C$_1$-C$_4$)-alkoxy-(C$_1$-C$_4$)-alkyl or tri-(C$_1$-C$_2$)-alkylsilyl, by preference (C$_1$-C$_4$)-alkyl, and $R^{28}$ is (C$_1$-C$_8$)-alkyl or (C$_1$-C$_4$)-haloalkyl, by preference C$_1$-haloalkyl.

Also especially preferred are safeners of the formula (II) where the symbols and indices have the following meaning:

W is (W4);

$R^{17}$ is halogen, nitro, (C$_1$-C$_4$)-alkyl, (C$_1$-C$_2$)-haloalkyl, by preference CF$_3$, or (C$_1$-C$_4$)-alkoxy;

n' is 0, 1, 2 or 3;

m' is 0 or 1;

$R^{18}$ is a radical of the formula OR$^{24}$;

$R^{24}$ is hydrogen, $(C_1-C_4)$-alkyl, carboxy-$(C_1-C_4)$-alkyl, $(C_1-C_4)$-alkoxycarbonyl-$(C_1-C_4)$-alkyl, by preference $(C_1-C_4)$-alkoxy-CO—CH$_2$—, $(C_1-C_4)$-alkoxy-CO—C(CH$_3$)(H)—, HO—CO—CH$_2$— or HO—CO—C(CH$_3$)(H)—, and $R^{29}$ is hydrogen, $(C_1-C_4)$-alkyl, $(C_1-C_4)$-haloalkyl, $(C_3-C_7)$-cycloalkyl or phenyl which is unsubstituted or substituted by one or more of the radicals selected from the group consisting of halogen, $(C_1-C_4)$-alkyl, $(C_1-C_4)$-haloalkyl, nitro, cyano and $(C_1-C_4)$-alkoxy.

The following groups of compounds are especially suitable for use as safeners for the herbicidally active substances of the formula (I):

a) Compounds of the dichlorophenylpyrazoline-3-carboxylic acid type (i.e. of the formula (II), where W=(W1) and $(R^{17})_n$=2,4-Cl$_2$), by preference compounds such as ethyl 1-(2,4-dichlorophenyl)-5-(ethoxy-carbonyl)-5-methyl-2-pyrazoline-3-carboxylate (II-1), and related compounds as they are described in WO-A 91/07874;

b) dichlorophenylpyrazolecarboxylic acid derivatives (i.e. of the formula (II), where W=(W2) and $(R^{17})_n$=2,4-Cl$_2$), by preference compounds such as ethyl 1-(2,4-dichlorophenyl)-5-methyl-pyrazole-3-carboxylate (II-2), ethyl 1-(2,4-dichlorophenyl)-5-isopropylpyrazole-3-carboxylate (II-3), ethyl 1-(2,4-dichlorophenyl)-5-(1,1-dimethylethyl)pyrazole-3-carboxylate (II-4), ethyl 1-(2,4-dichlorophenyl)-5-phenylpyrazole-3-carboxylate (II-5) and related compounds as they are described in EP-A-0 333 131 and EP-A-0 269 806.

c) Compounds of the triazolecarboxylic type (i.e. of the formula (II), where W=(W3) and $(R^{17})_n$=2,4-Cl$_2$), by preference compounds such as fenchlorazol, i.e. ethyl 1-(2,4-dichlorophenyl)-5-trichloromethyl-(1H)-1,2,4-triazole-3-carboxylate (II-6), and related compounds (see EP-A-0 174 562 and EP-A-0 346 620);

d) Compounds of the 5-benzyl- or 5-phenyl-2-isoxazoline-3-carboxylic acid type or the 5,5-diphenyl-2-isoxazoline-3-carboxylic acid type (where W=(W4)), by preference compounds such as ethyl 5-(2,4-dichlorobenzyl)-2-isoxazoline-3-carboxylate (II-7) or ethyl 5-phenyl-2-isoxazoline-3-carboxylate (II-8) and related compounds as they are described in WO-A-91/08202, or ethyl 5,5-diphenyl-2-isoxazoline-carboxylate (II-9) or n-propyl 5,5-diphenyl-2-isoxazoline-carboxylate (II-10) or ethyl 5-(4-fluorophenyl)-5-phenyl-2-isoxazoline-3-carboxylate (II-11), as they are described in WO-A-95/07897.

e) Compounds of the 8-quinolinoxyacetic acid type, for example those of the formula (III) where $(R^{19})_n$=5-Cl, $R^{20}$=OR$^{24}$ and T=CH$_2$, by preference the compounds
1-methyl(5-chloro-8-quinolinoxy)acetate (III-1),
1,3-dimethyl-but-1-yl(5-chloro-8-quinolinoxy)acetate (III-2),
4-allyloxybutyl(5-chloro-8-quinolinoxy)acetate (III-3),
1-allyloxyprop-2-yl(5-chloro-8-quinolinoxy)acetate (III-4),
ethyl(5-chloro-8-quinolinoxy)acetate (III-5),
methyl(5-chloro-8-quinolinoxy)acetate (III-6),
allyl(5-chloro-8-quinolinoxy)acetate (III-7),
2-(2-propylideneiminoxy)-1-ethyl(5-chloro-8-quinolinoxy)acetate (III-8),
2-oxo-prop-1-yl(5-chloro-8-quinolinoxy)acetate (III-9) and related compounds as they are described in EP-A-0 860 750, EP-A-0 094 349 and EP-A-0 191 736 or EP-A-0 492 366.

f) Compounds of the (5-chloro-8-quinolinoxy)malonic acid type, i.e. of the formula (III) where $(R^{19})_n$=5-Cl, $R^{20}$=OR$^{24}$, T=-CH(COO-alkyl)-, by preference the compounds diethyl(5-chloro-8-quinolinoxy)malonate, diallyl (5-chloro-8-quinolinoxy)malonate, methyl ethyl(5-chloro-8-quinolinoxy)malonate and related compounds as they are described in EP-A-0 582 198.

g) Compounds of the dichloroacetamide type, i.e. of the formula (IV), by preference:
N,N-diallyl-2,2-dichloroacetamide (dichlormid, from U.S. Pat. No. 4,137,070),
4-dichloroacetyl-3,4-dihydro-3-methyl-2H-1,4-benzoxazine (benoxacor, from EP 0 149 974),
N1,N2-diallyl-N2-dichloroacetylglycinamide (DKA-24, from HU 2143821),
4-dichloroacetyl-1-oxa-4-aza-spiro[4,5]decane (AD-67),
2,2-dichloro-N-(1,3-dioxolan-2-ylmethyl)-N-(2-propenyl)acetamide (PPG-1292),
3-dichloroacetyl-2,2,5-trimethyloxazolidine,
3-dichloroacetyl-2,2-dimethyl-5-phenyloxazolidine,
3-dichloroacetyl-2,2-dimethyl-5-(2-thienyl)oxazolidine,
3-dichloroacetyl-5-(2-furanyl)-2,2-dimethyloxazolidine (furilazole, MON 13900),
1-dichloroacetyl-hexahydro-3,3,8a-trimethylpyrrolo[1,2-a]pyrimidin-6(2H)-one (dicyclonon, BAS 145138), h) compounds of group B(b), by preference
1,8-naphthalic anhydride,
methyl diphenylmethoxyacetate,
cyanomethoxyimino(phenyl)acetonitrile (cyometrinil),
1,3-dioxolan-2-ylmethoxyimino(phenyl)acetonitrile (oxabetrinil),
4'-chloro-2,2,2-trifluoroacetophenone O-1,3-dioxolan-2-ylmethyloxime (fluxofenim),
4,6-dichloro-2-phenylpyrimidine (fenclorim),
benzyl 2-chloro-4-trifluoromethyl-1,3-thiazole-5-carboxylate (flurazole),
2-dichloromethyl-2-methyl-1,3-dioxolane (MG-191),
N-(4-methylphenyl)-N'-(1-methyl-1-phenylethyl)urea (dymrone),
1-[4-(N-2-methoxybenzoylsulfamoyl)phenyl]-3-methylurea,
1-[4-(N-2-methoxybenzoylsulfamoyl)phenyl]-3,3-dimethylurea,
1-[4-(N-4,5-dimethylbenzoylsulfamoyl)phenyl]-3-methylurea,
1-[4-(N-naphthoylsulfamoyl)phenyl]-3,3-dimethylurea,
(2,4-dichlorophenoxy)acetic acid (2,4-D),
(4-chlorophenoxy)acetic acid,
(R,S)-2-(4-chloro-o-tolyloxy)propionic acid (mecoprop),
4-(2,4-dichlorophenoxy)butyric acid (2,4-DB),
(4-chloro-o-tolyloxy)acetic acid (MCPA),
4-(4-chloro-o-tolyloxy)butyric acid,
4-(4-chlorophenoxy)butyric acid,
3,6-dichloro-2-methoxybenzoic acid (dicamba),
1-(ethoxycarbonyl)ethyl 3,6-dichloro-2-methoxybenzoate (lactidichlor),
and their salts and esters, by preference $(C_1-C_8)$.

Furthermore preferred as safeners are compounds of the formula (V) or salts thereof in which $R^{30}$ is hydrogen, $(C_1-C_6)$-alkyl, $(C_3-C_6)$-cycloalkyl, furanyl or thienyl, where each of the last-mentioned 4 radicals is unsubstituted or substituted by one or more substituents selected from the group consisting of halogen, $(C_1-C_4)$-alkoxy, halo-$(C_1-C_6)$-alkoxy and $(C_1-C_4)$-alkylthio and, in the case of cyclic radicals, also $(C_1-C_4)$-alkyl and $(C_1-C_4)$-haloalkyl, $R^{31}$ is hydrogen, $R^{32}$ is halogen, halo-$(C_1-C_4)$-alkyl, halo-$(C_1-C_4)$-alkoxy, $(C_1-C_4)$-alkyl, $(C_1-C_4)$-alkoxy, $(C_1-C_4)$-alkylsulfonyl, $(C_1-C_4)$-alkoxycarbonyl or $(C_1-C_4)$-alkylcarbonyl, by preference halogen, $(C_1-C_4)$-haloalkyl such as trifluoromethyl, $(C_1-C_4)$-alkoxy, halo-$(C_1-C_4)$-alkoxy, $(C_1-C_4)$-alkoxycarbonyl or $(C_1-C_4)$-alkylsulfonyl, $R^{33}$ is hydrogen, $R^{34}$ is halogen, $(C_1-C_4)$-alkyl, halo-$(C_1-C_4)$-alkyl, halo-$(C_1-C_4)$-alkoxy, $(C_3-C_6)$-cycloalkyl, phenyl, $(C_1-C_4)$-alkoxy, cyano, $(C_1-C_4)$-alkylthio, $(C_1-C_4)$-alkylsulfynyl, $(C_1-C_4)$-alkylsulfonyl, $(C_1-C_4)$-alkoxycarbonyl or $(C_1-C_4)$-alkylcarbonyl, by preference halogen, $(C_1-C_4)$-alkyl, $(C_1-C_4)$-haloalkyl such as trifluoromethyl, halo-$(C_1-C_4)$-alkoxy, $(C_1-C_4)$-alkoxy or $(C_1-C_4)$-alkylthio, n is 0, 1 or 2 and t is 1 or 2.

Furthermore preferred are safeners of the formula (VI) in which $X^3$ is CH;

$R^{35}$ is hydrogen, $(C_1-C_6)$-alkyl, $(C_3-C_6)$-cycloalkyl, $(C_2-C_6)$-alkenyl, $(C_5-C_6)$-cycloalkenyl, phenyl or 3- to 6-membered heterocyclyl having up to three hetero atoms selected from the group consisting of nitrogen, oxygen and sulfur, the six last-mentioned radicals optionally being substituted by one or more identical or different substituents selected from the group consisting of halogen, $(C_1-C_6)$-alkoxy, $(C_1-C_6)$-haloalkoxy, $(C_1-C_2)$-alkylsulfynyl, $(C_1-C_2)$-alkylsulfonyl, $(C_3-C_6)$-cycloalkyl, $(C_1-C_4)$-alkoxycarbonyl, $(C_1-C_4)$-alkylcarbonyl and phenyl and in the case of cyclic radicals, also $(C_1-C_4)$-alkyl and $(C_1-C_4)$-haloalkyl;

$R^{36}$ is hydrogen, $(C_1-C_6)$-alkyl, $(C_2-C_6)$-alkenyl, $(C_2-C_6)$-alkynyl, the three last-mentioned radicals optionally being substituted by one or more identical or different substituents selected from the group consisting of halogen, hydroxyl, $(C_1-C_4)$-alkyl, $(C_1-C_4)$-alkoxy and $(C_1-C_4)$-alkylthio;

$R^{37}$ is identical or different halogen, $(C_1-C_4)$-haloalkyl, $(C_1-C_4)$-haloalkoxy, nitro, $(C_1-C_4)$-alkyl, $(C_1-C_4)$-alkoxy, $(C_1-C_4)$-alkylsulfonyl, $(C_1-C_4)$-alkoxycarbonyl or $(C_1-C_4)$-alkylcarbonyl;

$R^{38}$ is hydrogen $R^{39}$ is identical or different halogen, nitro, $(C_1-C_4)$-alkyl, $(C_1-C_4)$-haloalkyl, $(C_1-C_4)$-haloalkoxy, $(C_3-C_6)$-cycloalkyl, phenyl, $(C_1-C_4)$-alkoxy, cyano, $(C_1-C_4)$-alkylthio, $(C_1-C_4)$-alkylsulfinyl, $(C_1-C_4)$-alkylsulfonyl, $(C_1-C_4)$-alkoxycarbonyl or $(C_1-C_4)$-alkylcarbonyl;

s is 0, 1 or 2 and o is 1 or 2.

The following sub-groups are particularly preferred amongst the safeners of the formula (VII):

compounds in which $R^{48}$ and $R^{49}$ are H, $(C_1-C_8)$-alkyl, phenyl, phenyl-$(C_1-C_8)$-alkyl, $(C_1-C_4)$-alkoxy-$(C_1-C_8)$-alkyl, $(C_3-C_6)$-alkenyl or $(C_3-C_6)$-alkynyl, it being possible for phenyl rings to be substituted by F, Cl, Br, $NO_2$, CN, $OCH_3$, $(C_1-C_4)$-alkyl or $CH_3-SO_2$;

compounds in which $R^g$ is H;

compounds in which A is $Y-R^h$;

compounds in which E is oxygen;

compounds in which $Q^1$ is $CR_2^{47}$;

compounds in which $R^{47}$ is hydrogen;

compounds where m"=1 and E is oxygen or sulfur;

compounds in which m"=0;

compounds in which $R^{40}$, $R^{41}$, $R^{42}$, $R^{43}$ and $R^{44}$ are in each case hydrogen, E is oxygen, $Q^1$ is $CR_2^{47}$, A is $Y-R^h$ and m"=1, in particular those where $R^{47}$ is H, $R^b$ is $CH_3$ and Y is oxygen;

compounds in which $Q^1$ is $CR_2^{47}$ and m" equals 0, in particular those in which $R^{44}$ and $R^{47}$ are hydrogen and A is $Y-R^h$, where $R^h$ is by preference methyl and Y is by preference oxygen.

Preferred groups of herbicides of the formula (I) are given in Tables 1 to 4. In these tables, the abbreviations used denote:

c-Pr=cyclopropyl Bz=benzoyl

Et=ethyl Me=methyl

Ph=phenyl

TABLE 1

(V = V1):

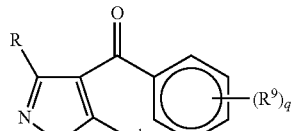

| Example No. | R | $R^1$ | $(R^9)_q$ |
|---|---|---|---|
| 1-1 | H | c-Pr | 2-$SO_2$Me-4-$CF_3$ |
| 1-2 | H | c-Pr | 2-$SO_2$Me-4-Cl |
| 1-3 | H | c-Pr | 2-Cl-4-$SO_2$Me |
| 1-4 | H | c-Pr | 2-$NO_2$-4-$SO_2$Me |
| 1-5 | H | c-Pr | 2,4-$Cl_2$-3-Me |
| 1-6 | H | c-Pr | 2,4-$Cl_2$ |
| 1-7 | H | c-Pr | 2-Cl-3-COOMe-4-$SO_2$Me |
| 1-8 | H | c-Pr | 2,4-$Br_2$ |
| 1-9 | H | c-Pr | 2,4-$Br_2$-3-$OCH_2$SMe |
| 1-10 | H | c-Pr | 2-$CF_3$-4-$SO_2$Me |
| 1-11 | H | c-Pr | 2-$SO_2$Me-4-Br |
| 1-12 | H | c-Pr | 2-Cl-3-OEt-4-$SO_2$Et |
| 1-13 | H | c-Pr | 3,4-$Cl_2$-$SO_2$Me |
| 1-14 | H | c-Pr | 2-SMe-4-$CF_3$ |
| 1-15 | H | c-Pr | 2-SMe-4-Br |
| 1-16 | H | c-Pr | 3,4-$Cl_2$-2-SMe |
| 1-17 | H | c-Pr | 4-$SF_5$ |
| 1-18 | COOEt | c-Pr | 2-$SO_2$Me-4-$CF_3$ |
| 1-19 | COOEt | c-Pr | 2-$SO_2$Me-4-Cl |
| 1-20 | COOEt | c-Pr | 2-$NO_2$-4-$SO_2$Me |
| 1-21 | COOEt | c-Pr | 2,4-$Cl_2$-3-Me |
| 1-22 | COOEt | c-Pr | 2,4-$Br_2$ |
| 1-23 | COOEt | c-Pr | 2,4-$Br_2$-3-$OCH_2$SMe |
| 1-24 | COOMe | c-Pr | 2-$SO_2$Me-4-$CF_3$ |
| 1-25 | COOMe | c-Pr | 2-$SO_2$Me-4-Cl |
| 1-26 | COOMe | c-Pr | 2-Cl-3-$CO_2$Me-4-$SO_2$Me |
| 1-27 | H | 1-Me-c-Pr | 2-$SO_2$Me-4-$CF_3$ |
| 1-28 | H | 1-Me-c-Pr | 2-$SO_2$Me-4-Cl |
| 1-29 | H | 1-Me-c-Pr | 2-Cl-4-$SO_2$Me |
| 1-30 | H | 1-Me-c-Pr | 2-$NO_2$-4-$SO_2$Me |
| 1-31 | H | 1-Me-c-Pr | 2,4-$Cl_2$-3-Me |
| 1-32 | H | 1-Me-c-Pr | 2,4-$Cl_2$ |
| 1-33 | H | 1-Me-c-Pr | 2-Cl-3-COOMe-4-$SO_2$Me |
| 1-34 | COOEt | 1-Me-c-Pr | 2-Cl-3-COOMe-4-$SO_2$Me |
| 1-35 | COOEt | 1-Me-c-Pr | 2-$SO_2$Me-4-$CF_3$ |
| 1-36 | COOEt | 1-Me-c-Pr | 2-$SO_2$Me-4-Cl |
| 1-37 | COOEt | 1-Me-c-Pr | 2-Cl-4-$SO_2$Me |
| 1-38 | COOEt | 1-Me-c-Pr | 2-$NO_2$-4-$SO_2$Me |
| 1-39 | $SO_2$Me | c-Pr | 2-$SO_2$Me-4-$CF_3$ |
| 1-40 | $SO_2$Me | c-Pr | 2-$SO_2$Me-4-Cl |
| 1-41 | SOMe | c-Pr | 2-$SO_2$Me-4-$CF_3$ |
| 1-42 | SOMe | c-Pr | 2-$SO_2$Me-4-Cl |
| 1-43 | $SO_2$Me | c-Pr | 2-$NO_2$-4-$SO_2$Me |
| 1-44 | SOMe | c-Pr | 2-$NO_2$-4-$SO_2$Me |
| 1-45 | $SO_2$Me | c-Pr | 2-Cl-4-$SO_2$Me |
| 1-46 | SOMe | c-Pr | 2-Cl-4-$SO_2$Me |
| 1-47 | COOMe | c-Pr | 2-SOMe-4-$CF_3$ |
| 1-48 | COOEt | c-Pr | 2-SOMe-4-$CF_3$ |
| 1-49 | H | c-Pr | 2-SOMe-4-$CF_3$ |
| 1-50 | $SO_2$Me | 1-Me-c-Pr | 2-$SO_2$Me-4-$CF_3$ |
| 1-51 | SOMe | 1-Me-c-Pr | 2-$SO_2$Me-4-$CF_3$ |
| 1-52 | $SO_2$Me | 1-Me-c-Pr | 2-$SO_2$Me-4-Cl |
| 1-53 | SOMe | 1-Me-c-Pr | 2-$SO_2$Me-4-Cl |

TABLE 2

(V = V2):

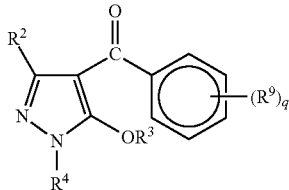

| Example No. | R² | R³ | R⁴ | $(R^9)_q$ |
|---|---|---|---|---|
| 2-1 | H | H | Et | 2-Cl-3-OEt-4-SO₂Et |
| 2-2 | H | H | Et | 2-SO₂Me-4-CF₃ |
| 2-3 | H | H | Et | 2-SO₂Me-4-Cl |
| 2-4 | H | H | Et | 2-SO₂Me-4-Br |
| 2-5 | H | H | Et | 2-CF₃-4-SO₂Me |
| 2-6 | H | H | Et | 2-Cl-4-SO₂Me |
| 2-7 | H | H | Et | 3,4-Cl₂-2-SO₂Me |
| 2-8 | H | H | Et | 2-Cl-3-COOMe-4-SO₂Me |
| 2-9 | H | H | Et | 2,4-Cl₂ |
| 2-10 | H | H | Et | 2-NO₂-4-SO₂Me |
| 2-11 | H | H | Et | 2,4-Br₂-3-OCH₂SMe |
| 2-12 | H | H | Et | 2,4-Br₂ |
| 2-13 | H | H | Me | 2-SO₂Me-4-CF₃ |
| 2-14 | H | H | Me | 2-SO₂Me-4-Cl |
| 2-15 | H | H | Me | 2,4-Br₂-3-OCH₂SMe |
| 2-16 | H | H | Me | 2,4-Cl₂ |
| 2-17 | H | H | Me | 2-SO₂Me-4-Cl |
| 2-18 | Me | CH₂—CO-(4-Me—Ph) | Me | 2,4-Cl₂-Cl-3-Me |
| 2-19 | Me | CH₂—CO-(4-Me—Ph) | Me | 2-SO₂Me-4-CF₃ |
| 2-20 | Me | CH₂—CO-(4-Me—Ph) | Me | 2-SO₂Me-4-Cl |
| 2-21 | Me | CH₂—CO-(4-Me—Ph) | Me | 2,4-Br₂-3-OCH₂SMe |
| 2-22 | Me | CH₂—CO-(4-Me—Ph) | Me | 2,4-Cl₂ |
| 2-23 | Me | CH₂—CO-(4-Me—Ph) | Me | 2,4-Br₂ |
| 2-24 | Me | CH₂—CO-(4-Me—Ph) | Me | 2-SO₂Me-4-Cl |
| 2-25 | Me | CH₂—CO-(4-Me—Ph) | Me | 2-Cl-3-COOMe-4-SO₂Me |
| 2-26 | Me | CH₂—CO-(4-Me—Ph) | Me | 2-NO₂-4-SO₂Me |
| 2-27 | Me | SO₂-(4-Me—Ph) | Me | 2,4-Cl₂ |
| 2-28 | Me | SO₂-(4-Me—Ph) | Me | 2,4-Br₂ |
| 2-29 | Me | SO₂-(4-Me—Ph) | Me | 2,4-Cl₂-3-Me |
| 2-30 | Me | SO₂-(4-Me—Ph) | Me | 2-SO₂Me-4-CF₃ |
| 2-31 | Me | SO₂-(4-Me—Ph) | Me | 2-SO₂Me-4-Cl |
| 2-32 | Me | SO₂-(4-Me—Ph) | Me | 2,4-Br₂-3-OCH₂SMe |
| 2-33 | Me | SO₂-(4-Me—Ph) | Me | 2-NO₂-4-SO₂Me |
| 2-34 | Me | CH₂—CO—Ph | Me | 2,4-Cl₂ |
| 2-35 | Me | CH₂—CO—Ph | Me | 2,4-Cl₂-3-Me |
| 2-36 | Me | CH₂—CO—Ph | Me | 2-SO₂Me-4-CF₃ |
| 2-37 | Me | CH₂—CO—Ph | Me | 2-SO₂Me-4-Cl |
| 2-38 | Me | CH₂—CO—Ph | Me | 2,4-Br₂-3-OCH₂SMe |
| 2-39 | Me | CH₂—CO—Ph | Me | 2-Cl-3-COOMe-4-SO₂Me |
| 2-40 | Me | CH₂—CO—Ph | Me | 2,4-Br₂ |
| 2-41 | Me | CH₂—CO—Ph | Me | 2-NO₂-4-SO₂Me |
| 2-42 | H | Bz | Me | 2,4-Cl₂ |
| 2-43 | H | Bz | Me | 2,4-Cl₂-3-Me |
| 2-44 | H | Bz | Me | 2-SO₂Me-4-CF₃ |
| 2-45 | H | Bz | Me | 2-SO₂Me-4-Cl |
| 2-46 | H | Bz | Me | 2,4-Br₂ |
| 2-47 | H | Bz | Me | 2-NO₂-4-SO₂Me |
| 2-48 | H | Bz | Me | 2-Cl-3-COOMe-4-SO₂Me |
| 2-49 | H | Bz | Me | 2,4-Br₂-3-OCH₂SMe |

TABLE 3

(V = V3):

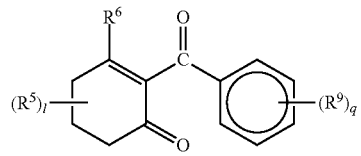

| Example No. | $(R^5)_l$ | R⁶ | $(R^9)_q$ |
|---|---|---|---|
| 3-1 | — | OH | 2-Cl-4-SO₂Me |
| 3-2 | — | OH | 2-NO₂-4-SO₂Me |
| 3-3 | — | OH | 2,4-Cl₂ |
| 3-4 | — | OH | 2,4-Br₂ |
| 3-5 | — | OH | 2,4-Cl₂-3-Me |
| 3-6 | — | OH | 2,4-Br₂-3-OCH₂SMe |
| 3-7 | — | OH | 2-SO₂Me-4-Cl |
| 3-8 | — | OH | 2-SO₂Me-4-CF₃ |
| 3-9 | — | OH | 2-SO₂Me-4-Br |
| 3-10 | — | OH | 2-Cl-3-COOMe-4-SO₂Me |
| 3-11 | — | OH | 2-NO₂-4-OCF₂H |
| 3-12 | 4,4-(Me)₂ | OH | 2-NO₂-4-OCF₂H |
| 3-13 | 4,4-(Me)₂ | OH | 2-Cl-4-SO₂Me |
| 3-14 | 4,4-(Me)₂ | OH | 2-NO₂-4-SO₂Me |
| 3-15 | 4,4-(Me)₂ | OH | 2,4-Cl₂ |
| 3-16 | 4,4-(Me)₂ | OH | 2-Cl-3-COOMe-4-SO₂Me |
| 3-17 | 4,4-(Me)₂ | OH | 2,4-Br₂-3-OCH₂SMe |
| 3-18 | 4,4-(Me)₂ | OH | 2-SO₂Me-4-Cl |
| 3-19 | 4,4-(Me)₂ | OH | 2-SO₂Me-4-CF₃ |
| 3-20 | 4,4-(Me)₂ | OH | 2,4-Cl₂-3-Me |
| 3-21 | 4,4-(Me)₂ | OH | 2,4-Br₂ |
| 3-22 | 4-CH₂—CH₂-6 | SPh | 2-Cl-4-SO₂Me |
| 3-23 | 4-CH₂—CH₂-6 | SPh | 2,4-Cl₂-3-Me |
| 3-24 | 4-CH₂—CH₂-6 | SPh | 2,4-Br₂-3-OCH₂SMe |
| 3-25 | 4-CH₂—CH₂-6 | SPh | 2-NO₂-4-SO₂Me |
| 3-26 | 4-CH₂—CH₂-6 | SPh | 2,4-Cl₂ |
| 3-27 | 4-CH₂—CH₂-6 | SPh | 2-SO₂Me-4-Cl |
| 3-28 | 4-CH₂—CH₂-6 | SPh | 2,4-Br₂ |
| 3-29 | 4-CH₂—CH₂-6 | SPh | 2-Cl-3-COOMe-4-SO₂Me |
| 3-30 | 4-CH₂—CH₂-6 | SPh | 2-SO₂Me-4-CF₃ |
| 3-31 | 5,5-(Me)₂ | OH | 2-NO₂-4-OCF₂H |
| 3-32 | 5,5-(Me)₂ | OH | 2-Cl-4-SO₂Me |
| 3-33 | 5,5-(Me)₂ | OH | 2-NO₂-4-SO₂Me |
| 3-34 | 5,5-(Me)₂ | OH | 2-Cl-3-COOMe-4-SO₂Me |
| 3-35 | 5,5-(Me)₂ | OH | 2,4-Cl₂-3-Me |
| 3-36 | 5,5-(Me)₂ | OH | 2,4-Cl₂ |
| 3-37 | 5,5-(Me)₂ | OH | 2,4-Br₂ |
| 3-38 | 5,5-(Me)₂ | OH | 2,4-Br₂-3-OCH₂SMe |
| 3-39 | 5,5-(Me)₂ | OH | 2-SO₂Me-4-Cl |
| 3-40 | 5,5-(Me)₂ | OH | 2-SO₂Me-4-CF₃ |

TABLE 4

(V = V4):

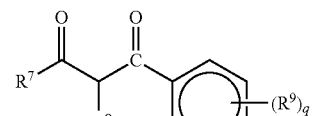

| Example No. | R⁷ | R⁸ | $(R^9)_q$ |
|---|---|---|---|
| 4-1 | c-Pr | CN | 2-Cl-3-OEt-4-SO₂Et |
| 4-2 | c-Pr | CN | 2-SO₂Me-4-CF₃ |
| 4-3 | c-Pr | CN | 2-SO₂Me-4-Cl |
| 4-4 | c-Pr | CN | 2-SO₂Me-4-Br |
| 4-5 | c-Pr | CN | 2-CF₃-4-SO₂Me |
| 4-6 | c-Pr | CN | 2-Cl-4-SO₂Me |
| 4-7 | c-Pr | CN | 3,4-Cl₂-2-SO₂Me |
| 4-8 | c-Pr | CN | 2,4-Cl₂ |
| 4-9 | c-Pr | CN | 2,4-Br₂ |
| 4-10 | c-Pr | CN | 2-Cl-3-COOMe-4-SO₂Me |
| 4-11 | c-Pr | CN | 2,4-Cl₂-3-Me |

TABLE 4-continued (V = V4):

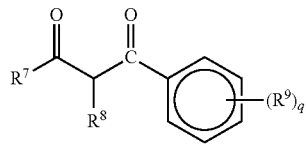

| Example No. | $R^7$ | $R^8$ | $(R^9)_q$ |
|---|---|---|---|
| 4-12 | c-Pr | CN | 2,4-$Br_2$-3-$OCH_2$SMe |
| 4-13 | c-Pr | CN | 2-$NO_2$-4-$SO_2$Me |

The safeners (antidotes) of the formulae (II)-(VII) and the compounds of group (b), for example safeners of the abovementioned groups a) to h), reduce or prevent phytotoxic effects which may occur when using the herbicidally active substances of the formula (I) in crops of useful plants without substantially affecting the efficacy of these herbicidally active substances against harmful plants. This allows the field of application of conventional crop protection products to be widened quite considerably and to be extended to, for example, crops such as wheat, barley, maize, rice and other crops in which a use of the herbicides was hitherto impossible, or only limited, that is to say at low rates and with a restricted spectrum.

The herbicidally active substances and the abovementioned safeners can be applied together (as a readymix or by the tank mix method) or in succession in any desired sequence. The weight ratio of safener: herbicidally active substance may vary within wide limits and is preferably within the range from 1:100 to 100:1, in particular from 1:10 to 10:1. The optimum amounts of herbicidally active substance and safener in each case depend on the type of the herbicidally active substance used or on the safener used and on the species of the crop stand to be treated and can be determined in each individual case by simple, routine preliminary experiments.

The main fields of application for the combinations according to the invention are, in particular, maize and cereal crops (for example wheat, rye, barley, oats), rice, sorghum, but also cotton and soybeans, preferably cereals, rice and maize.

Depending on their properties, the safeners employed in accordance with the invention can be used for pretreating the seeds of a crop plant (seed dressing), or be incorporated into the seed furrows prior to sowing or applied together with the herbicide before or after plant emergence. The pre-emergence treatment includes not only the treatment of the area under cultivation prior to sowing and the treatment of the areas under cultivation where the seeds have been planted but the plants have not yet emerged. The joint application with the herbicide is preferred. To this end, tank mixes or readymixes can be employed.

The application rates of safener required may vary within wide limits depending on the indication and the herbicidally active substance used and are generally in the range of from 0.001 to 5 kg, preferably 0.005 to 0.5 kg, of active substance per hectare.

The present invention therefore also relates to a method of protecting crop plants from phytotoxic side effects of herbicides of the formula (I), which comprises applying an antidote-effective amount of a compound of the formula (II), (III), (IV), (V), (VI), (VII) and/or (selected from group (b)) to the plants, the seeds of the plants or the area under cultivation, either before, after or simultaneously with the herbicidally active substance A of the formula (I).

The herbicide/safener combination according to the invention may also be employed for controlling harmful plants in crops of genetically engineered plants which are either known or still to be developed. As a rule, the transgenic plants are distinguished by particular, advantageous properties, for example by resistances to certain crop protection agents, resistances to plant diseases or pathogens causing plant diseases such as particular insects or microorganisms such as fungi, bacteria or viruses. Other particular properties relate for example, to the harvested material in terms of quantity, quality, storing properties, composition and specific constituents. Thus, transgenic plants are known which have an increased starch content or an altered starch quality, or those where the harvested material has a different fatty acid composition.

The use of the combinations according to the invention in economically important transgenic crops of useful plants and ornamentals, for example cereals such as wheat, barley, rye, oats, panic grasses, rice, cassava and maize or else crops of sugar beet, cotton, soya, oilseed rape, potatoes, tomatoes, peas and other types of vegetables.

When the combinations according to the invention are applied in transgenic crops, effects on harmful plants to be observed in other crops are frequently accompanied by effects which are specific for application in the transgenic crop in question, for example an altered or specifically widened weed spectrum which can be controlled, altered application rates which may be used, preferably good compatibility with the herbicides to which the transgenic crop is resistant, and altered growth and yield of the transgenic crop plants.

The invention therefore also relates to the use of the combination according to the invention for controlling harmful plants in transgenic crop plants.

The safeners of the formulae (III)-(VII) and of group (b) and their combinations with one or more of the abovementioned herbicidally active substances of the formula (II) can be formulated in various ways, depending on the biological and/or chemico-physical parameters specified. Examples of suitable formulations which are possible are: wettable powders (WP), emulsifiable concentrates (EC), water-soluble powders (SP), water-soluble concentrates (SL), concentrated emulsions (BW) such as oil-in-water and water-in-oil emulsions, sprayable solutions or emulsions, capsule suspensions (CS), oil- or water-based dispersions (SC), suspoemulsions, suspension concentrates, dusts (DP), oil-miscible solutions (OL), seed treatment products, granules (GR) in the form of microgranules, spray granules, coated granules and adsorption granules, granules for soil application or broadcasting, water-soluble granules (SG), water-dispersible granules (WG), ULV formulations, microcapsules and waxes.

These individual formulation types are known in principle and described, for example, in: Winnacker-Küchler, "Chemische Technologie" [Chemical Engineering], Volume 7, C. Hauser Verlag Munich, $4^{th}$ Edition 1986; Wade van Valkenburg, "Pesticide Formulations", Marcel Dekker N.Y., 1973; K. Martens, "Spray Drying Handbook", $3^{rd}$ Ed. 1979, G. Goodwin Ltd. London.

The formulation auxiliaries which may be required, such as inert materials, surfactants, solvents and other additives are also known and described, for example, in: Watkins, "Handbook of Insecticide Dust Diluents and Carriers", $2^{nd}$ Ed., Darland Books, Caldwell N.J., H.v. Olphen, "Introduction to Clay Colloid Chemistry", $2^{nd}$ Ed., J. Wiley & Sons, N.Y.; C. Marsden, "Solvents Guide", $2^{nd}$ Ed., Interscience, N.Y. 1963;

McCutcheon's "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schönfeldt, "Grenzflächenaktive Äthylenoxidaddukte" [Surface-active Ethylene Oxide Adducts], Wiss. Verlagsgesell., Stuttgart 1976; Winnacker-Küchler, "Chemische Technologie" [Chemical Engineering], Volume 7, C. Hauser Verlag Munich, 4$^{th}$ Edition 1986.

Based on these formulations, it is also possible to prepare combinations with other substances which act as crop protection agents, such as insecticides, acaricides, herbicides, fungicides, and also with safeners, fertilizers and/or growth regulators, for example in the form of a readymix or as a tank mix.

Wettable powders are preparations which are uniformly dispersible in water and which, besides the active substance, also comprise ionic and/or nonionic surfactants (wetting agents, dispersants), for example polyoxyethylated alkylphenols, polyoxyethylated fatty alcohols, polyoxyethylated fatty amines, fatty alcohol polyglycol ether sulfates, alkanesulfonates, alkylbenzenesulfonates, sodium lignosulfonate, sodium 2,2'-dinaphthylmethane-6,6'-disulfonate, sodium dibutylnaphthalene-sulfonate, or else sodium oleoylmethyltaurinate, in addition to a diluent or inert substance. To prepare the wettable powders, the herbicidally active substances are ground finely, for example in customary apparatus such as hammer mills, blower mills and air-jet mills, and they are simultaneously or subsequently mixed with the formulation auxiliaries.

Emulsifiable concentrates are prepared, for example, by dissolving the active substance in an organic solvent such as butanol, cyclohexanone, dimethylformamide, xylene, or else higher-boiling saturated or unsaturated aliphatic or aromatic, or mixtures of the organic solvents with the addition of one or more ionic and/or nonionic surfactants (emulsifiers). Examples of substances which can be used as emulsifiers are: calcium ($C_6$-$C_{18}$)-alkylarylsulfonates such as calcium dodecylbenzenesulfonate, or nonionic emulsifiers such as fatty acid polyglycol esters, ($C_2$-$C_{18}$)-alkylarylpolyglycol ethers, fatty alcohol polyglycol ethers, propylene oxide/ethylene oxide condensates, alkyl polyethers, sorbitan esters, such as sorbitan fatty acid esters or polyoxyethylene sorbitan esters such as polyoxyethylene sorbitan fatty acid esters.

Dusts are generally obtained by grinding the active substance with finely divided solid substances, for example talc, natural clays such as kaolin, bentonite and pyrophyllite, or diatomaceous earth.

Suspension concentrates can be water- or oil-based. They can be prepared, for example, by wet-grinding using commercially available bead mills with or without addition of surfactants, for example those which have already been mentioned above in the case of the other formulation types.

Emulsions, for example oil-in-water emulsions (EW), can be prepared, for example, by means of stirrers, colloid mills and/or static mixers using aqueous organic solvents in the presence or absence of surfactants which have already been mentioned above, for example, in the case of the other formulation types.

Granules can be prepared either by spraying the active substance onto adsorptive, granulated inert material or by applying active substance concentrates to the surface of carriers such as sand, kaolinites or granulated inert material with the aid of binders, for example polyvinyl alcohol, sodium polyacrylate or else mineral oils. Suitable active substances can also be granulated in the manner which is conventional for the preparation of fertilizer granules, if desired as a mixture with fertilizers. As a rule, water-dispersible granules are prepared by the customary processes such as spray-drying, fluidized-bed granulation, disk granulation, mixing with high-speed mixers and extrusion without solid inert material. For the preparation of disk, fluidized-bed, extruder and spray granules see, for example, "Spray-Drying Handbook" 3$^{rd}$ ed. 1979, G. Goodwin Ltd., London; J. E. Browning, "Agglomeration", Chemical and Engineering 1967, pages 147 et seq.; "Perry's Chemical Engineer's Handbook", 5$^{th}$ Ed., McGraw-Hill, New York 1973, pp. 8-57.

For further details in the formulation of crop protection products see, for example, G. C. Klingman, "Weed Control as a Science", John Wiley and Sons, Inc., New York, 1961, pages 81-96 and J. D. Freyer, S. A. Evans, "Weed Control Handbook", 5$^{th}$ Ed., Blackwell Scientific Publications, Oxford, 1968, pages 101-103.

As a rule, the agrochemical formulations comprise 0.1 to 99% by weight, in particular 0.1 to 95% by weight, of active substances of the formulae (II)-(VII) and/or (b) or of the herbicide/antidote mixture of active substances (I) and (II)-(VII) and/or (b) and 1 to 99.9% by weight, in particular 5 to 99.8% by weight, of a solid or liquid additive and 0 to 25% by weight, in particular 0.1 to 25% by weight, of a surfactant.

In wettable powders, the active substance concentration is, for example, approximately 10 to 90% by weight, the remainder to 100% by weight being composed of customary formulation components. In the case of emulsifiable concentrates, the active substance concentration is approximately 1 to 80% by weight. Formulations in the form of dusts comprise approximately 1 to 20% by weight of active substance, sprayable solutions approximately 0.2 to 20% by weight of active substance. In the case of granules such as water-dispersible granules, the active substance content depends partly on whether the active compound is in liquid or solid form. The active substance content of the water-dispersible granules is, as a rule, between 10 and 90% by weight.

Besides this, the abovementioned formulations of active substances may comprise, if appropriate, the adhesives, wetters, dispersants, emulsifiers, penetrants, preservatives, antifreeze agents, solvents, fillers, carriers, colorants, antifoams, evaporation inhibitors and pH and viscosity regulators which are customary in each case.

Components which can be used for the mixtures according to the invention in mixed formulations or in a tank mix are, for example, known active substances as they are described, for example, in Weed Research 26, 441-445 (1986), or "The Pesticide Manual", 10$^{th}$ edition, The British Crop Protection Council, 1994, and in the literature cited therein. Herbicides which are known from the literature and which can be combined with the mixtures according to the invention are, for example, the following active substances (note: either the common names in accordance with the International Organization for Standardization (ISO) or the chemical names, if appropriate together with the customary code number, of the compounds are given):

acetochlor; acifluorfen; aclonifen; AKH 7088, i.e. [[[1-[5-[2-chloro-4-(trifluoromethyl)-phenoxy]-2-nitrophenyl]-2-methoxyethylidene]-amino]-oxy]-acetic acid and its methyl ester; alachlor; alloxydim; ametryn; amidosulfuron; amitrol; AMS, i.e. ammonium sulfamate; anilofos; asulam; atrazine; azafenidine (DPX-R6447), azimsulfurone (DPX-A8947); aziprotryn; barban; BAS 516 H, i.e. 5-fluoro-2-phenyl-4H-3,1-benzoxazin-4-one; benazolin; benfluralin; benfuresate; bensulfuron-methyl; bensulide; bentazone; benzofluor; benzoylprop-ethyl; benzthiazuron; bialaphos; bifenox; bispyribac-natrium (KIH-2023), bromacil; bromobutide; bromofenoxim; bromoxynil; bromuron; buminafos; busoxinone; butachlor; butamifos; butenachlor; buthidazole; butralin; butroxydim (ICI-0500), butylate; cafenstrole (CH-900); carbetamide; cafentrazone; CDAA, i.e. 2-chloro-N,N-di-2-propenylacetamide; CDEC, i.e. 2-chloroallyl diethyldithiocarbamate; chlomethoxyfen; chloramben; chloransulam-methyl (XDE-565), chlorazifop-butyl, chlorbromuron; chlorbufam; chlorfenac; chlorflurecol-methyl; chloridazon; chlorimuron-ethyl; chlornitrofen; chlorotoluron; chloroxuron; chlorpropham; chlorsulfuron; chlorthal-dimethyl; chlorthiamid; cinidon-ethyl, cinmethylin; cinosulfuron; clethodim; clodinafop and its ester derivatives (for example clodinafop-propargyl); clomazone; clomeprop; cloproxydim; clopyralid; cumyluron (JC 940); cyanazine; cycloate; cyclosulfamuron (AC 014); cycloxydim; cycluron; cyhalofop and its ester derivatives (for example the butyl ester, DEH-112); cyperquat; cyprazine; cyprazole; 2,4-DB; dalapon; desmedipham; desmetryn; di-allate; dicamba; dichlobenil; dichlorprop; diclofop and its esters such as diclofopmethyl; diclosulam (XDE-564), diethatyl; difenoxuron; difenzoquat; diflufenican; diflufenzopyrnatrium (SAN-835H), dimefuron; dimethachlor; dimethametryn; dimethenamid (SAN-582H); dimethazone, methyl 5-(4,6-dimethylpyrimidin-2-yl-carbamoylsulfamoyl)-1-(2-pyridyl)-pyrazole-4-carboxylate (NC-330); triaziflam (IDH-1105), clomazon; dimethipin; dimetrasulfuron, dinitramine; dinoseb; dinoterb; diphenamid; dipropetryn; diquat; dithiopyr; diuron; DNOC; eglinazine-ethyl; EL 177, i.e. 5-cyano-1-(1,1-dimethylethyl)-N-methyl-1H-pyrazole-4-carboxamide; endothal; epoprodan (MK-243), EPTC; esprocarb; ethalfluralin; ethametsulfuron-methyl; ethidimuron; ethiozin; etofumesate; F5231, i.e. N-[2-chloro-4-fluoro-5-[4-(3-fluoropropyl)-4,5-dihydro-5-oxo-1H-tetrazol-1-yl]-phenyl]-ethanesulfonamide; ethoxyfen and its ester (for example ethyl ester, HN-252); ethoxysulfuron (from EP 342569) etobenzanid (HW 52); 3-(4-ethoxy-6-ethyl-1,3,5-triazin-2-yl)-1-(2,3-dihydro-1,1-dioxo-2-methylbenzo[b]thiophen-7-sulfonyl)urea (EP-A 079 683); 3-(4-ethyl-6-methoxy-1,3,5-triazin-2-yl)-1-(2,3-dihydro-1,1-dioxo-2-methylbenzo[b]thiophen-7-sulfonyl)urea (EP-A 079 683); fenoprop; fenoxan, fenoxaprop and fenoxaprop-P and their esters, for example fenoxaprop-P-ethyl and fenoxapropethyl; fenoxydim; fenuron; flamprop-methyl; flazasulfuron; flufonacet (BAY-FOE-5043), fluazifop and fluazifop-P, florasulam (DE-570) and their esters, for example fluazifop-butyl and fluazifop-P-butyl; fluchloralin; flumetsulam; flumeturon; flumiclorac and its esters (for example pentyl ester, S-23031); flumioxazin (S-482); flumipropyn; flupoxam (KNW-739); fluorodifen; fluoroglycofen-ethyl; flupropacil (UBIC-4243); sodium flupyrsulfuron-methyl (DPX-KE459), fluridone; flurochloridone; fluroxypyr; flurtamone; fluthiacet-methyl (KIN-9201), fomesafen; fosamine; furyloxyfen; glufosinate; glyphosate; halosafen; halosulfuron and its esters (for example methyl ester, NC-319); haloxyfop and its esters; haloxyfop-P (=R-haloxyfop) and its esters; hexazinone; imazamethabenz-methyl; imazamox (AC-299263), imazapyr; imazaquin and salts such as the ammonium salt; imazethamethapyr; imazethapyr; imazosulfuron; iodosulfuron (methyl 4-iodo-2-[3-(4-methoxy-6-methyl-1,3,5-triazin-2-yl)ureidosulfonyl]benzoate, sodium salt, WO 92/13845); ioxynil; isocarbamid; isopropalin; isoproturon; isouron; isoxaben; isoxapyrifop; karbutilate; lactofen; lenacil; linuron; MCPA; MCPB; mecoprop; mefenacet; mefluidid; metamitron; metazachlor; methabenzthiazuron; metham; methazole; methoxyphenone; methyldymrone; metabenzuron, methyl 2-[3-(4,6-dimethoxypyrimidin-2-yl)ureidosulfonyl]-4-methanesulfonamidomethylbenzoate (WO 95/10507); methobenzuron; metobromuron; metolachlor; S-metolachlor, metosulam (XRD 511); metoxuron; metribuzin; metsulfuron-methyl; MH; molinate; monalide; monocarbamide dihydrogensulfate; monolinuron; monuron; MT 128, i.e. 6-chloro-N-(3-chloro-2-propenyl)-5-methyl-N-phenyl-3-pyridazinamine;

MT 5950, i.e. N-[3-chloro-4-(1-methylethyl)-phenyl]-2-methylpentanamide; N,N-dimethyl-2-[3-(4,6-dimethoxypyrimidin-2-yl)ureidosulfonyl]-4-formyl-amino-benzamide (WO 95/01344); naproanilide; napropamide; naptalam; NC 310, i.e. 4-(2,4-dichlorobenzoyl)-1-methyl-5-benzyloxypyrazole; neburon; nicosulfuron; nipyraclophen; nitralin; nitrofen; nitrofluorfen; norflurazon; orbencarb; oryzalin; oxadiargyl (RP-020630); oxadiazon; oxaziclomefone (MY-100), oxyfluorfen; oxasulfuron (CGA-277476), paraquat; pebulate; pendimethalin; pentoxazone (KPP-314), perfluidone; phenisopham; phenmedipham; picloram; piperophos; piributicarb; pirifenop-butyl; pretilachlor; primisulfuron-methyl; procyazine; prodiamine; profluralin; proglinazine-ethyl; prometon; prometryn; propachlor; propanil; propaquizafop and its esters; propazine; propham; propisochlor; propyzamide; prosulfalin; prosulfocarb; prosulfuron (CGA-152005); prynachlor; pyraflufen-ethyl (ET-751), pyrazon; pyrazosulfuron-ethyl; pyrazoxyfen; pyribenzoxim, pyridate; pyriminobac-methyl (KIN-6127), pyrithiobac (KIH-2031); pyroxofop and its esters (for example propargyl ester); quinclorac; quinmerac; quinofop and its ester derivatives, quizalofop and quizalofop-P and their ester derivatives, for example quizalofop-ethyl; quizalofop-P-tefuryl and -ethyl; renriduron; rimsulfuron (DPX-E 9636); S 275, i.e. 2-[4-chloro-2-fluoro-5-(2-propynyloxy)-phenyl]-4,5,6,7-tetrahydro-2H-indazole; secbumeton; sethoxydim; siduron; simazine; simetryn; SN 106279, i.e. 2-[[7-[2-chloro-4-(trifluoro-methyl)-phenoxy]-2-naphthalenyl]-oxy]-propanoic acid and its methyl ester; sulfentrazone (FMC-97285, F-6285); sulfazuron; sulfometuran-methyl; sulfosate (ICI-A0224); sulfosulfuron (MON-37500), TCA; tebutam (GCP-5544); tebuthiuron; tepraloxidim (BAS-620H), terbacil; terbucarb; terbuchlor; terbumeton; terbuthylazine; terbutryn; TFH 450, i.e. N,N-diethyl-3-[(2-ethyl-6-methylphenyl)-sulfonyl]-1H-1,2,4-triazole-1-carboxamide; thenylchlor (NSK-850); thiazafluron; thiazopyr (Mon-13200); thidiazimin (SN-124085); thifensulfuron-methyl; thiobencarb; tiocarbazil; tralkoxydim; tri-allate; triasulfuron; triazofenamide; tribenuron-methyl; triclopyr; tridiphane; trietazine; trifluralin; triflusulfuron and esters (for example methyl ester, DPX-66037); trimeturon; tsitodef; vernolate; WL 110547, i.e. 5-phenoxy-1-[3-(trifluoromethyl)-phenyl]-1H-tetrazole; UBH-509; D-489; LS 82-556; KPP-300; KPP-421, MT-146, NC-324; KH-218; DPX-N8189; DOWCO-535; OK-8310; V-53482; PP-600; MBH-001.

For use, the formulations which are in commercially available form are, if desired, diluted in the customary manner, for example using water in the case of wettable powders, emulsifiable concentrates, dispersions and water-dispersible granules. Preparations in the form of dusts, soil granules, granules for broadcasting and sprayable solutions are usually not diluted any further with other inert substances prior to use.

The necessary application rate of the herbicides of the formula (I) varies with the external conditions such as, inter alia, temperature, humidity, and the nature of the herbicide used. It may be varied within wide limits, for example between 0.001 and 10.0 kg/ha or more of herbicide, but it is preferably between 0.005 and 5 kg/ha.

The examples which follow are intended to illustrate the invention:

A. Formulation Examples a) A dust is obtained by mixing 10 parts by weight of a compound of the formula (II)-(VII) and/or from amongst group B (b) or of an active substance mixture of a herbicidally active substance of the formula (I) and a safener of the formula (II)-(VII) and/or from amongst group (b) and 90 parts by weight of talc as inert substance and comminuting the mixture in a hammer mill.

b) A wettable powder which is readily dispersible in water is obtained by mixing 25 parts by weight of a compound of the formula (II)-(VII) and/or from amongst group B(b) or of an active substance mixture of a herbicidally active substance of the formula (I) and a safener of the formula (II)-(VII) and/or from amongst group B(b), 64 parts by weight of kaolin-containing quartz as inert substance, 10 parts by weight of potassium lignosulfonate and 1 part by weight of sodium oleoylmethyltaurinate as wetter and dispersant, and grinding the mixture in a pinned-disk mill.

c) A concentrate which is readily dispersible or suspensible in water is obtained by mixing 20 parts by weight of a compound of the formula (II)-(VII) and/or from amongst group B(b) or of an active substance mixture of a herbicidally active substance of the formula (I) and a safener of the formula (II)-(VII) and/or from amongst group B(b), 6 parts by weight of alkylphenol polyglycol ether (®Triton X 207), 3 parts by weight of isotridecanol polyglycol ether (8 EO) and 71 parts by weight of paraffinic mineral oil (boiling range, for example, approx. 255 to above 277° C.) and grinding the mixture in a ball mill to a fineness of below 5 microns.

d) An emulsifiable concentrate is obtained from 15 parts by weight of a compound of the formula (II)-(VII) and/or from amongst group B(b) or of an active substance mixture of a herbicidally active substance of the formula (I) and a safener of the formula (II)-(VII) and/or from amongst group B(b), 75 parts by weight of cyclohexanone as solvent and 10 parts by weight of oxethylated nonylphenol as emulsifier.

e) Water-dispersible granules are obtained by mixing 75 parts by weight of a compound of the formula (II)-(VII) and/or from amongst group B(b) or of an active substance mixture of a herbicidally active substance of the formula (I) and a safener of the formula (II)-(VII) and/or from amongst group B(b)
10 parts by weight of calcium lignosulfonate,
5 parts by weight of sodium lauryl sulfate,
3 parts by weight of polyvinyl alcohol and
7 parts by weight of kaolin,
grinding the mixture on a pinned-disk mill and granulating the powder in a fluidized bed by spraying on water as granulation liquid.

f) Water-dispersible granules are also obtained by homogenizing and precomminuting, in a colloid mill,
25 part(s) by weight of a compound of the formula (II)-(VII) and/or from amongst groups B(b) or of an active substance mixture of a herbicidally active substance of the formula (I) and a safener of the formula (II)-(VII) and/or from amongst group B(b)
5 parts by weight of sodium 2,2'-dinaphthylmethane-6,6'-disulfonate,
2 parts by weight of sodium oleoylmethyltaurinate,
1 parts by weight of polyvinyl alcohol,
17 parts by weight of calcium carbonate and
50 parts by weight of water,
subsequently grinding the mixture on a bead mill and atomizing and drying the resulting suspension in a spray tower by means of a single-substance nozzle.

BIOLOGICAL EXAMPLES

1. Greenhouse Experiments
1.1 Pre-Emergence

Seeds or rhizome pieces of monocotyledonous and dicotyledonous harmful plants and useful plants are placed in sandy loam in pots of 9 to 13 cm diameter and covered with soil. As an alternative, for the rice test, rice plants and harmful plants which are undesired in this crop of useful plant, are grown in a waterlogged soil. Various doses of the herbicides and safeners formulated as emulsifiable concentrates or dusts were applied to the surface of the soil cover in the form of aqueous dispersions or suspensions or emulsions at a rate of 300 to 800 l of water/ha (converted), or, in the case of the rice test, poured into the irrigation water. The pots are then kept in the greenhouse under optimal conditions to grow the plants on. 3-4 weeks after the treatment, the damage to useful plants and harmful plants is scored visually. The damage is expressed in percentages in comparison with untreated controls.

The test results are compiled in Tables 5 and 6 (a.i.=active ingredient).

TABLE 5

| Application rate: 200-400 g a.i./ha; herbicide 1-1; maize | | | |
|---|---|---|---|
| Product | Application rate | Phytotoxicity on maize [%] | |
| Herbicide/safener | [g a.i./ha] | Variety Felix | Variety Dea |
| Herbicide 1-1 | 400 | 85 | 80 |
| Herbicide 1-1 | 300 | 85 | 85 |
| Herbicide 1-1 | 200 | 78 | 78 |
| Herbicide 1-1/safener b-1 | 300 + 300 | 50 | 40 |
| Herbicide 1-1/safener c-1 | 300 + 300 | 70 | 55 |
| Herbicide 1-1/safener c-3 | 300 + 300 | 45 | 45 |
| Herbicide 1-1/safener c-7 | 300 + 300 | 35 | 25 |
| Herbicide 1-1/safener c-10 | 300 + 300 | 40 | 38 |

TABLE 6

| Application rate: 100-300 g a.i./ha; herbicide 1-1; action against grass weeds/broad-leaved weeds | | | | | |
|---|---|---|---|---|---|
| Product Herbicide/ | Application rate | Action [%] | | | |
| safener | [g a.i./ha] | ECHCG | SETVI | ABUTH | PHBPU |
| Herbicide 1-1 | 300 | 99 | 100 | 98 | 90 |
| Herbicide 1-1/safener b-1 | 300 + 300 | 99 | 100 | 99 | 90 |
| Herbicide 1-1/safener c-1 | 300 + 300 | 99 | 100 | 98 | 85 |

Herbicide 1-1: Herbicide Example No. 1-1 (Table 1)
Safener b-1: 1-[4-(2-Methoxybenzoylsulfamoyl)phenyl]-3-methylurea
Safener c-1: 2-Methoxy-N-[4-(2-methoxybenzoylsulfamoyl)phenyl]-acetamide
Safener c-3: N-[4-(2-Methoxybenzoylsulfamoyl)phenyl]-cyclobutane-carboxamide
Safener c-7: N-[4-(2-Chlorobenzoylsulfamoyl)phenyl]-cyclopropane-carboxamide
Safener c-10: N-[4-(2-Trifluoromethoxybenzoylsulfamoyl)phenyl]-cyclo-propanecarboxamide ECHCG: *Echinocloa crus galli*
ABUTH: *Abutilon theophrasti*
PHBPU: *Pharbitis purpureum*
SETVI: *Setaria viridis*

1.2 Post-Emergence

Seeds or rhizome pieces of monocotyledonous and dicotyledonous harmful plants and useful plants are placed in sandy loam in pots of 9 to 13 cm diameter and covered with soil. As an alternative, for the rice test, rice plants and harmful plants which are undesired in this crop of useful plants are grown in a waterlogged soil. In the three-leaf stage, i.e. approximately three weeks after the experiment was set up, various dosages of the herbicides and safeners, formulated as emulsifiable concentrates or dusts, are sprayed in the form of aqueous dispersions or suspensions or emulsions on the green parts of the plant at an application rate of 300 to 800 l of water/ha (converted) or, in the rice test, also poured into the irrigation water. To grow the plants on, the pots are kept in the greenhouse under optimal conditions. The damage to useful plants and harmful plants is assessed visually 2-3 weeks after the treatment. The test results are compiled in Tables 7 to 9.

TABLE 7

Application rate: 100-300 g a.i./ha; herbicide 3-1; wheat

| Product Herbicide/safener | Dose [kg a.i./ha] | Damage [%] Wheat (variety Ralle) |
|---|---|---|
| Herbicide 3-1 | 300 | 40 |
| Herbicide 3-1 | 200 | 35 |
| Herbicide 3-1 | 100 | 30 |
| Herbicide 3-1/safener II-9 | 300 + 150 | 10 |
| Herbicide 3-1/safener II-9 | 200 + 100 | 5 |
| Herbicide 3-1/safener II-9 | 100 + 50 | 0 |
| Herbicide 3-2 | 300 | 45 |
| Herbicide 3-2 | 200 | 30 |
| Herbicide 3-2 | 100 | 30 |
| Herbicide 3-2/safener II-9 | 300 + 300 | 10 |
| Herbicide 3-2/safener II-9 | 200 + 200 | 0 |
| Herbicide 3-2/safener II-9 | 100 + 100 | 0 |

TABLE 8 pplication rate: 100-300 g a.i./ha; herbicide 1-1; maize

| Product | Application rate | Phytotoxicity to maize [%] | |
|---|---|---|---|
| Herbicide/safener | A[g a.i./ha] | Variety Felix | Variety Dea |
| Herbicide 1-1 | 100 | 13 | 15 |
| Herbicide 1-1 | 300 | 45 | 30 |
| Herbicide 1-1/safener b-1 | 300 + 300 | 13 | 3 |
| Herbicide 1-1/safener c-1 | 300 + 300 | 5 | 18 |
| Herbicide 1-1/safener II-9 | 300 + 300 | 10 | 20 |

TABLE 9

Application rate: 500 g a.i./ha; herbicide 3-1; maize

| Product | Application rate | Phytotoxicity to maize [%] | |
|---|---|---|---|
| Herbicide/safener | [g a.i./ha] | Variety Felix | Variety Dea |
| Herbicide 3-1 | 500 | 23 | 15 |
| Herbicide 3-1/safener c-1 | 500 + 500 | 10 | 0 |
| Herbicide 3-1/safener II-9 | 500 + 500 | 5 | 0 |
| Herbicide 3-1/safener II-9 | 500 + 1000 | 0 | 0 |

Herbicide 1-1: Herbicide Example No. 1-1 (Table 1)
Herbicide 3-1: Herbicide Example No. 3-1 (Table 3)
Herbicide 3-2: Herbicide Example No. 3-2 (Table 3)
Safener II-9: Ethyl 5,5-diphenyl-2-isoxazoline-3-carboxylate
Safener b-1: 1-[4-(2-Methoxybenzoylsulfamoyl)phenyl]-3-methylurea
Safener c-1: 2-Methoxy-N-[4-(2-methoxybenzoylsulfamoyl)phenyl]-acetamide 2. Field Experiments The field experiments were carried out in plots of 8 to 10 m², and each experiment was carried out in 2 to 4 replications. After the crop plants had been sown, the test preparations were applied pre-emergence, or in the 2-6-leaf stage, using plot sprayers. The spray volume was 100-300 l water/ha; it was applied by means of flat-jet nozzles at a pressure of 2-3 bar. Evaluation was done by visual scoring. The effects on the crop plants or on the broad-leaved weeds/grass weeds were estimated in comparison with untreated control plots using a percentage scale (0-100%). After application, the plants were scored 3-4 times at intervals of approx. 14, 28, 42 days after application. The results represent averages over 2-4 replications. In general, crop damage in the case of maize is acceptable up to approximately 15%. Anti-weed action should show efficacies of ≥60%. From sowing until the experiments were concluded, they were exposed to the natural weather conditions (precipitation, temperature, atmospheric humidity, insolation), as they are characteristic for the experimental sites.

The test results are compiled in Tables 10 to 13 (dat: days after treatment).

TABLE 10

Field trial: Application in the 4-leaf stage, maize (post-emergence)

| Product | Application rate | Phytotoxicity to maize [%] | |
|---|---|---|---|
| Herbicide/safener | [g a.i./ha] | 14 dat | 31 dat |
| Herbicide 1-1 | 105 | 35 | 12 |
| Herbicide 1-1/safener II-9 | 105 + 100 | 7 | 0 |
| Safener II-9 | 100 | 0 | 0 |

TABLE 11

Field trial: Application in the 4-leaf stage, maize

| Product | Application rate | Phytotoxicity to maize [%] | |
|---|---|---|---|
| Herbicide/safener | [g a.i./ha] | 14 dat | 42 dat |
| Herbicide 1-1 | 50 | 42 | 18 |
| Herbicide 1-1/safener II-9 | 50 + 120 | 8 | 2 |
| Safener II-9 | 120 | 0 | 0 |

TABLE 12

Action on grass weeds/broad-leaved weeds (post-emergence)

| Product | Application rate | Phytotoxicity [%] | | | |
|---|---|---|---|---|---|
| Herbicide/safener | [g a.i./ha] | Maize | *Panicum minor* | *Setaria faberi* | *Abutilon theophrastis* |
| Herbicide 1-1 | 105 | 35 | 75 | 75 | 72 |
| Herbicide 1-1/safener II-9 | 105 + 100 | 7 | 72 | 83 | 73 |
| Safener II-9 | 100 | 0 | 0 | 0 | 0 |

TABLE 13

| | Mixture with sulfonylureas (post-emergence) | | |
|---|---|---|---|
| | Application rate | Phytotoxicity to maize [%] | |
| Product Herbicide/safener | [g a.i./ha] | 14 dat | 42 dat |
| Herbicide 1-1 | 50 | 42 | 18 |
| Herbicide 2 | 120 | 13 | 7 |
| Herbicide 1-1 + herbicide 2 + safener II-9 | 50 + 120 + 120 | 10 | 5 |
| Safener II-9 | 120 | 0 | 0 |

Herbicide 1-1: Herbicide Example No. 1-1 (Table 1)
Herbicide 2: N,N-Dimethyl-2-[3-(4,6-dimethoxypyrimidin-2-yl)ureido-sulfonyl]-4-formylaminobenzamide
Safener II-9: Ethyl 5,5-diphenyl-2-isoxazoline-3-carboxylate

We claim:

1. A herbicidally active composition comprising a mixture of:
   A. a herbicidally active amount of a compound of the formula 3-2:

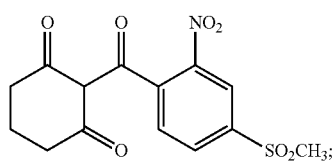

and
   B. an antidote-effective amount of a compound of the formula (II):

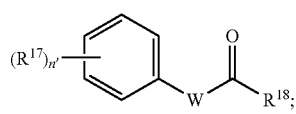

where the symbols and indices have the following meanings:
   W is (W4);

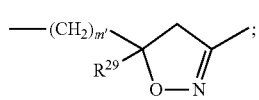

where:
   m' is 0; and
   $R^{29}$ is hydrogen, $(C_1-C_4)$alkyl, $(C_1-C_4)$haloalkyl, $(C_3-C_7)$cycloalkyl, or phenyl, which is unsubstituted or substituted by one or more radicals selected from the group consisting of halogen, $(C_1-C_4)$alkyl, $(C_1-C_4)$haloalkyl, nitro, cyano, and $(C_1-C_4)$alkoxy;
   $R^{17}$ is halogen, nitro, $(C_1-C_4)$alkyl, $(C_1-C_2)$haloalkyl, or $(C_1-C_4)$alkoxy;
   n' is 0, 1, 2, or 3; and
   $R^{18}$ is a radical of the formula $OR^{24}$;
      where $R^{24}$ is hydrogen, $(C_1-C_4)$alkyl, carboxy$(C_1-C_4)$alkyl, or $(C_1-C_4)$-alkoxycarbonyl$(C_1-C_4)$alkyl.

2. The herbicidally active composition as claimed in claim 1;
   wherein a weight ratio of compound A: compound B is 1:100 to 100:1.

3. The herbicidally active composition as claimed in claim 1, further comprising:
   a further herbicide.

4. The herbicidally active composition as claimed in claim 2, further comprising:
   a further herbicide.

5. The herbicidally active composition as claimed in claim 3;
   wherein the further herbicide is a sulfonylurea.

6. The herbicidally active composition as claimed in claim 4;
   wherein the further herbicide is a sulfonylurea.

7. A method of controlling harmful plants in crops of useful plants, comprising:
   applying a herbicidally active amount of a herbicidally active composition as claimed in one of claims 1 to 6 to the harmful plants, the crop plants, seeds of the crop plants, or an area on which the crop plants grow.

8. The method as claimed in claim 7;
   wherein the crop plants belong to the group consisting of maize, wheat, rye, barley, oats, rice, sorghum, cotton, and soya.

9. The method as claimed in claim 7;
   wherein the crop plants are genetically altered plants.

10. The method as claimed in claim 8;
    wherein the crop plants are genetically altered plants.

11. A herbicidally active composition comprising a mixture of:
    A. a herbicidally active amount of a compound of the formula 3-2:

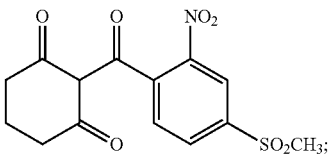

and
    B. an antidote-effective amount of a compound of the formula (II-9):

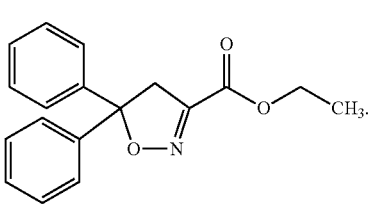

\* \* \* \* \*